(12) United States Patent
Danielsen et al.

(10) Patent No.: US 9,012,142 B2
(45) Date of Patent: *Apr. 21, 2015

(54) SEQUENCE-SPECIFIC DETECTION OF NUCLEOTIDE SEQUENCES

(75) Inventors: Mark Danielsen, Germantown, MD (US); Eugene A. Davidson, Boynton Beach, FL (US); Kenneth L. Dretchen, North Potomac, MD (US); Traci K. Pals, Alexandria, VA (US)

(73) Assignee: Georgetown University, Washington, DC (US)

( * ) Notice: Subject to any disclaimer, the term of this patent is extended or adjusted under 35 U.S.C. 154(b) by 1655 days.

This patent is subject to a terminal disclaimer.

(21) Appl. No.: 11/884,366

(22) PCT Filed: Feb. 15, 2006

(86) PCT No.: PCT/US2006/005248
§ 371 (c)(1),
(2), (4) Date: May 27, 2008

(87) PCT Pub. No.: WO2006/088910
PCT Pub. Date: Aug. 24, 2006

(65) Prior Publication Data
US 2011/0123980 A1 May 26, 2011

Related U.S. Application Data

(60) Provisional application No. 60/652,743, filed on Feb. 15, 2005, provisional application No. 60/758,196, filed on Jan. 12, 2006.

(51) Int. Cl.
| C12Q 1/68 | (2006.01) |
| C12P 19/34 | (2006.01) |
| C12N 9/00 | (2006.01) |
| C12M 1/34 | (2006.01) |

(52) U.S. Cl.
CPC ............ *C12Q 1/6823* (2013.01); *C12Q 1/6818* (2013.01)

(58) Field of Classification Search
USPC ............... 435/6.1, 91.2, 183, 287.2; 536/24.3
See application file for complete search history.

(56) References Cited

U.S. PATENT DOCUMENTS

| 5,656,430 A | 8/1997 | Chirikjian et al. |
| 5,763,178 A | 6/1998 | Chirikjian et al. |
| 5,763,181 A | 6/1998 | Han et al. |
| 5,846,726 A * | 12/1998 | Nadeau et al. ................... 435/6 |
| 6,548,247 B1 | 4/2003 | Chirikjian et al. |
| 6,787,304 B1 | 9/2004 | Han et al. |
| 6,884,586 B2 | 4/2005 | Van Ness et al. |
| 7,112,422 B2 | 9/2006 | Han et al. |
| 7,112,423 B2 | 9/2006 | Van Ness et al. |
| 2004/0142369 A1 * | 7/2004 | Alajem et al. ................... 435/6 |
| 2005/0214809 A1 * | 9/2005 | Han ................................ 435/6 |

OTHER PUBLICATIONS

Schoske et al, Multiplex PCR design strategy used for the simultaneous amplification of 10 Y chromosome short tandem repeat (STR) loci., 2003, Anal. Bioanal. Chem., 375, 333-343.*
De Preter et al, Application of laser capture microdisection in genetic analysis of neuroblastoma and neuroblastoma precursor cells, 2003, Cancer Letters, 197, 53-61.*
Stephens et al, Genome sequence of an obligate pathogen in humans: *Chlamydia trachomatis*, 1998, Science, 282, 754-759.*
Xu et al, Engineering a nicking endonuclease N.Alwl by domain swapping, 2001, PNAS, 98, 12990-12995.*
Data sheet N.BstNBI—New England Biolabs, down loaded from the internet [www.neb.com], pp. 1-3, printed on Jan. 2, 2014.*
Kiesling et al, Sequence specific detection of DNA using nicking endonuclease signal amplification (NESA), 2007, Nucleic Acids Research, 35, e117, pp. 1-9.*
Cairns et al., Biochemical and Biophysical Research Communications, 318(3):684-90 (2004).
PCT/US06/05248 International Search Report mailed Jul. 9, 2008 by Narayan K. Bhat.

* cited by examiner

*Primary Examiner* — Narayan Bhat
(74) *Attorney, Agent, or Firm* — RatnerPrestia

(57) ABSTRACT

A method for detecting the presence of a target nucleotide sequence in a sample of DNA is described herein in which a test sample comprising single stranded DNA is exposed to a DNA probe and a nicking endonuclease under conditions that would permit sequence-specific hybridization of the probe to a complementary target sequence. The probe comprises a sequence complementary to the target sequence to be detected and this sequence also includes a recognition sequence for the nicking endonuclease. If the sample contains the target sequence, the probe hybridizes to the target and is cleaved by the nicking endonuclease, which leaves the target intact. Observing the presence of probe cleaved by the nicking endonuclease indicates the presence of the target nucleotide sequence in the sample of DNA.

22 Claims, 17 Drawing Sheets

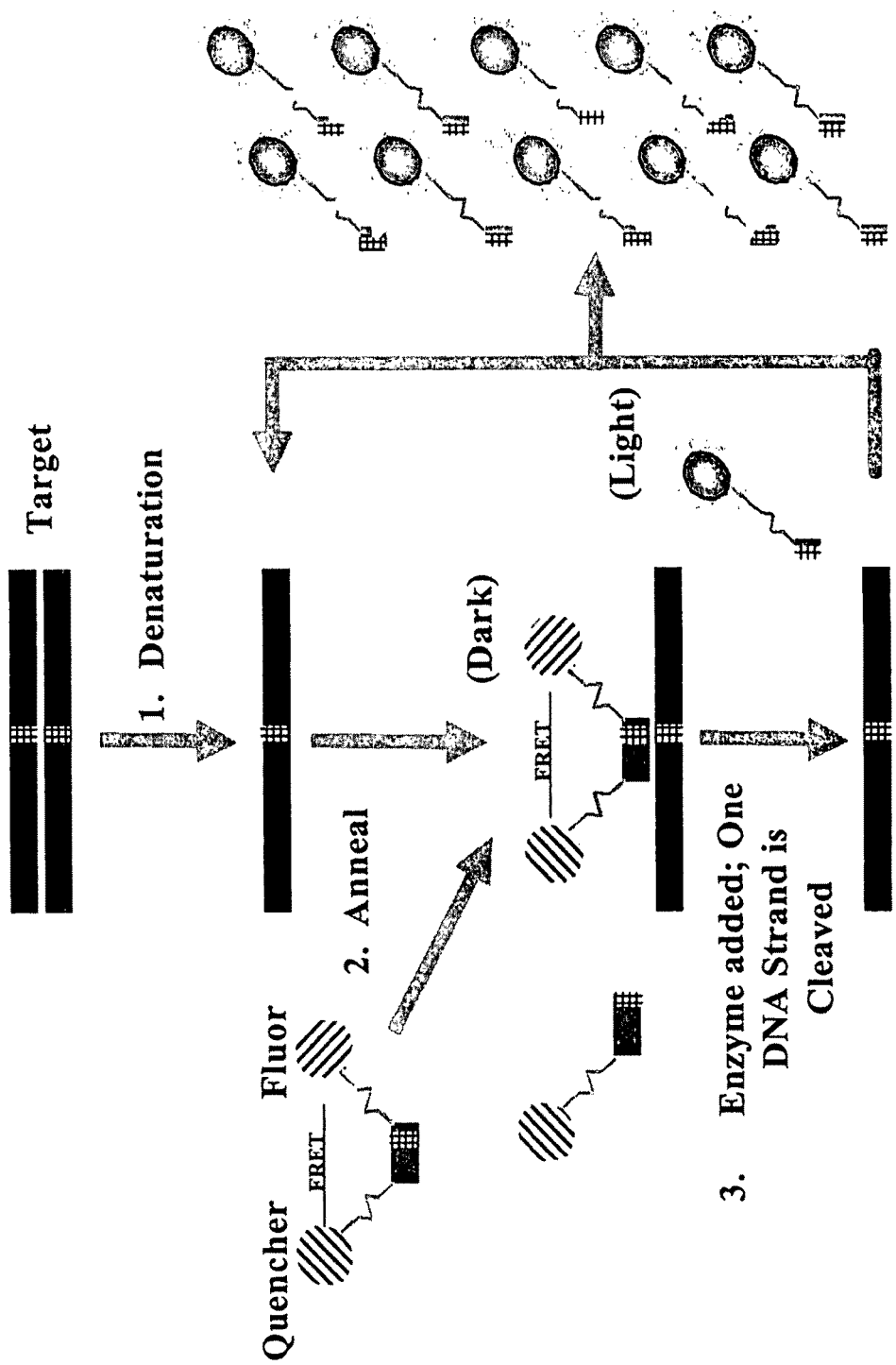

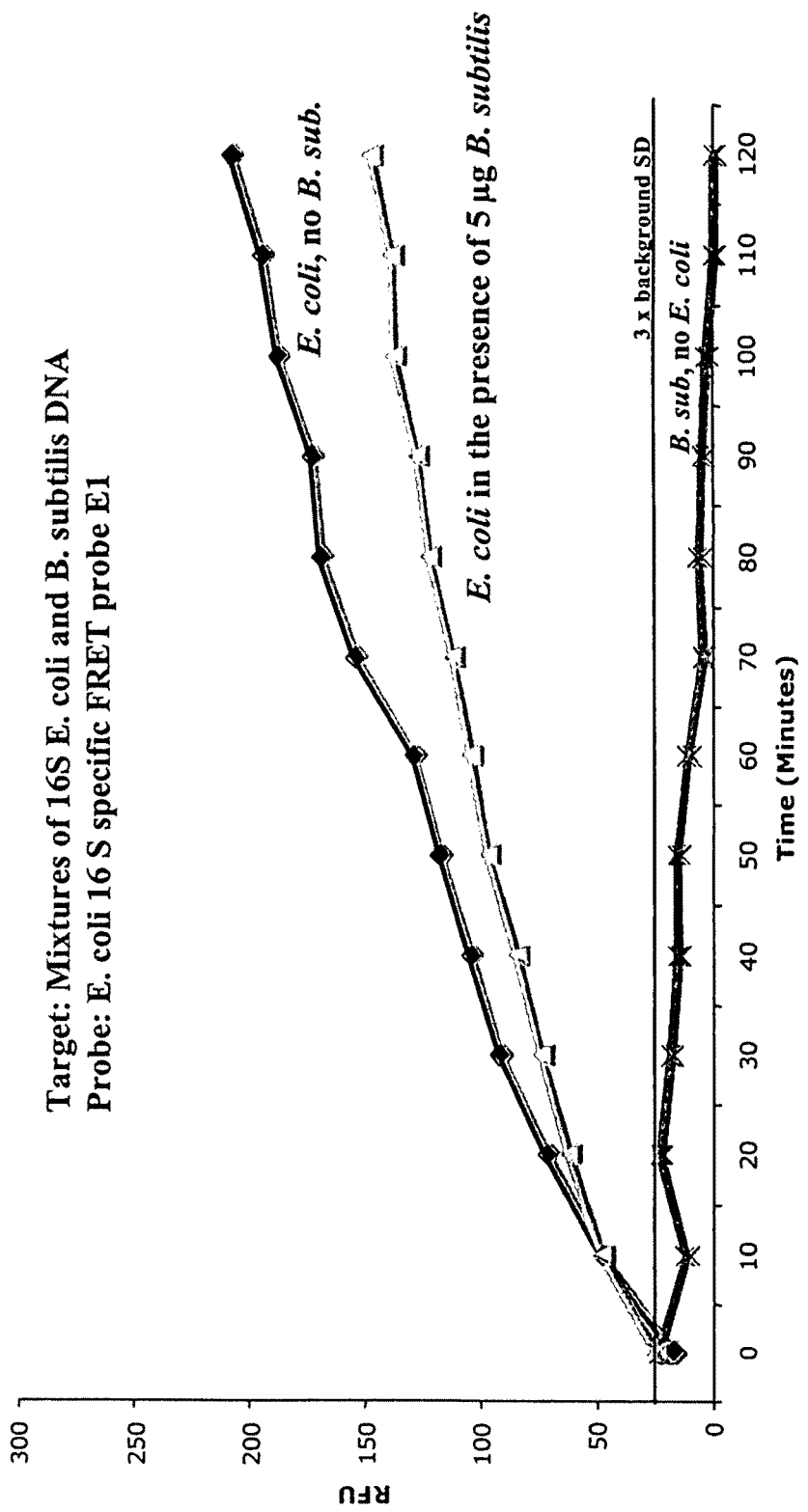

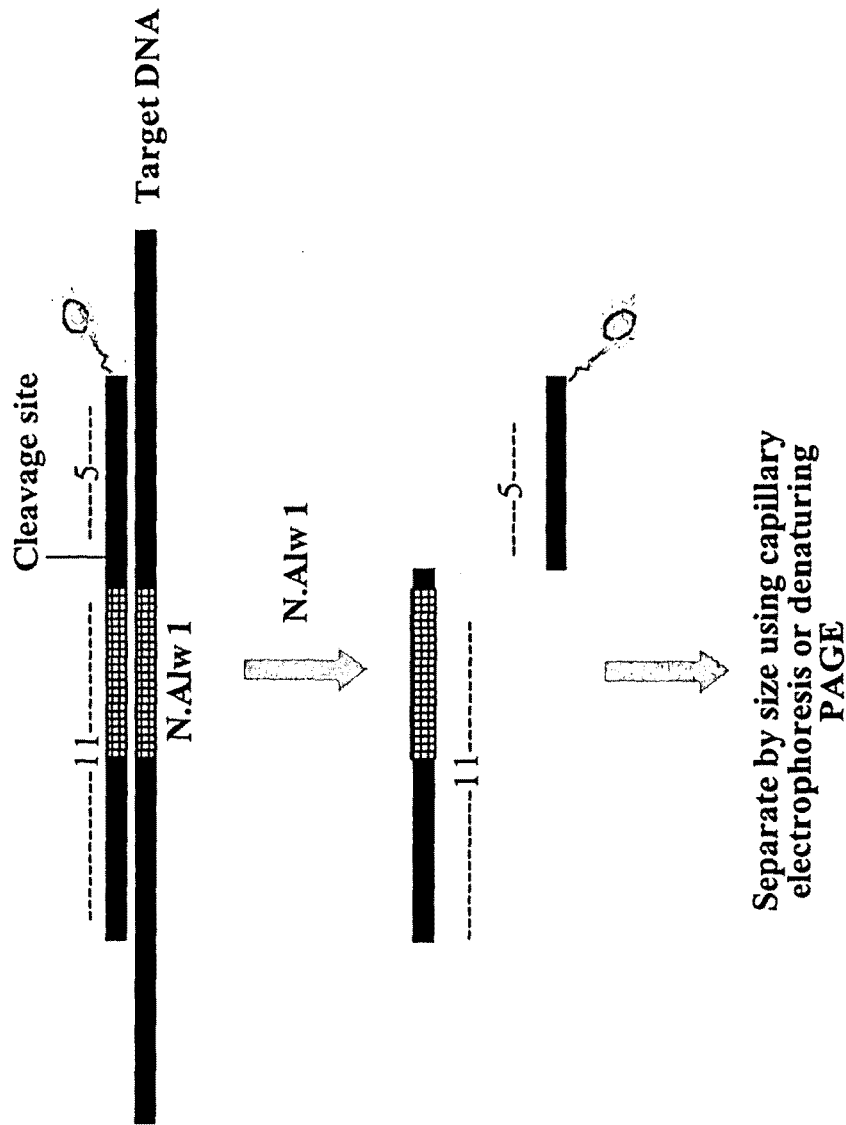

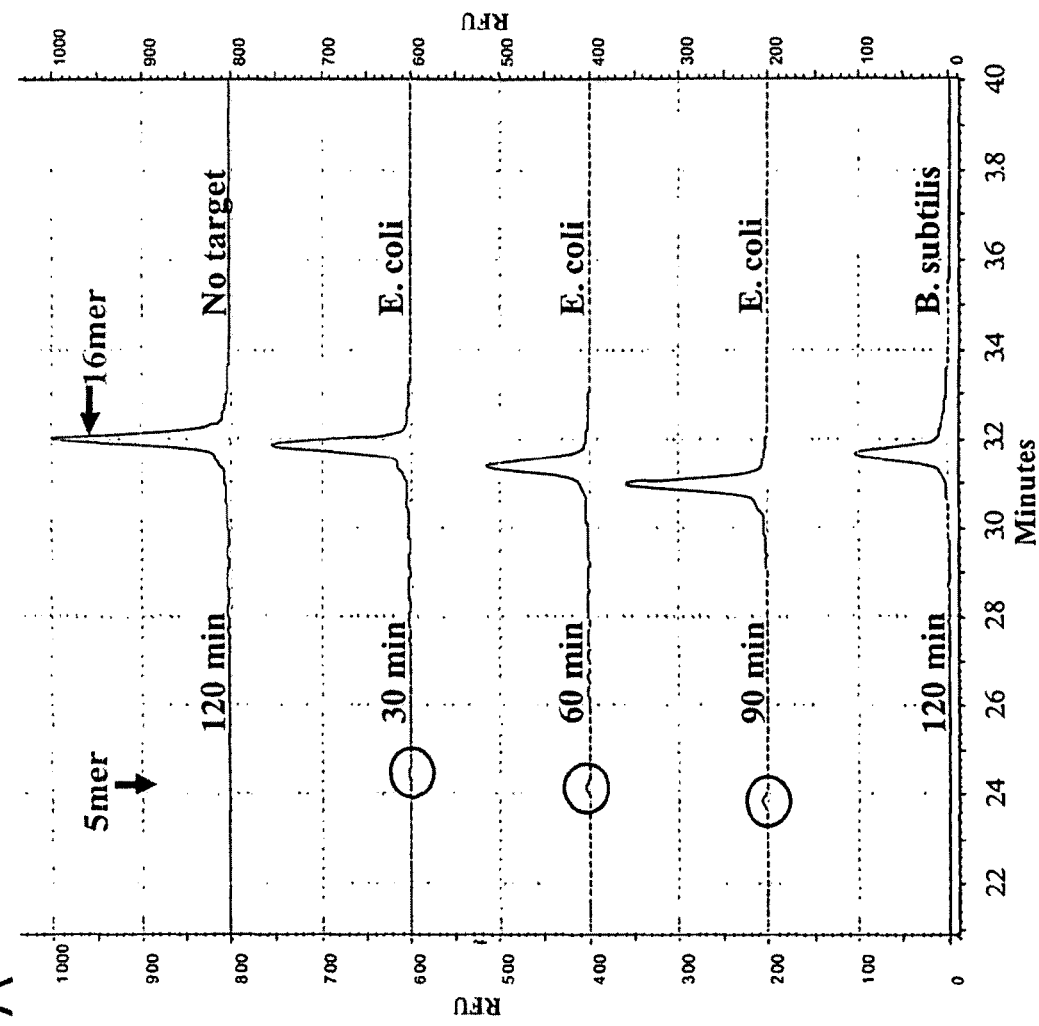
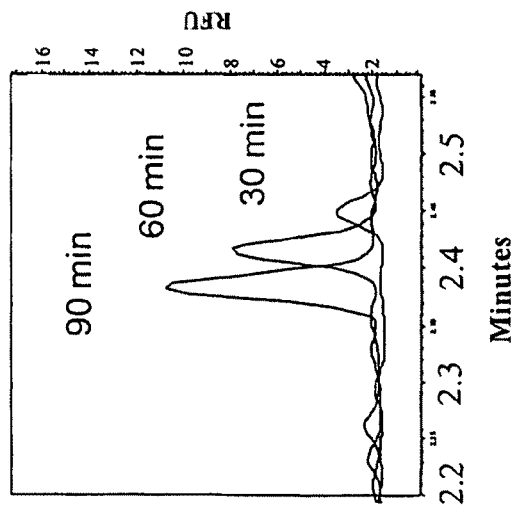
Figure 5

Figure 6

| 16 S DNA | Mutation | Probe | 50 | 55 | 56 | 57 | 58 | 59 | 60 | 60.6 | 62.5 |
|---|---|---|---|---|---|---|---|---|---|---|---|
| | | Temperature °C | 50 | 55 | 56 | 57 | 58 | 59 | 60 | 60.6 | 62.5 |
| | | E. coli (wt) E1c | | | | | | | | | |
| | | B. subtilis (wt) B1c | | | | | | | | | |
| T | A | E1c m1 | | | | | | | | | |
| G | C | E1c m2 | | | | | | | | | |
| G | C | E1c m3 | | | | | | | | | |
| C | G | E1c m4 | | | | | | | | | |
| A | T | E1c m5 | | | | | | | | | |
| T | A | E1c m6 | | | | | | | | | |
| T | A | E1c m7 | | | | | | | | | |
| C | G | E1c m8 | | | | | | | | | |
| T | A | E1c m9 | | | | | | | | | |
| G | C | E1c m10 | | | | | | | | | |
| A | T | E1c m11 | | | | | | | | | |
| T | A | E1c m12 | | | | | | | | | |
| C | G | E1c m13 | | | | | | | | | |
| C | G | E1c m14 | | | | | | | | | |
| A | T | E1c m15 | | | | | | | | | |
| C | G | E1cmp m16 | | | | | | | | | |

Figure 8
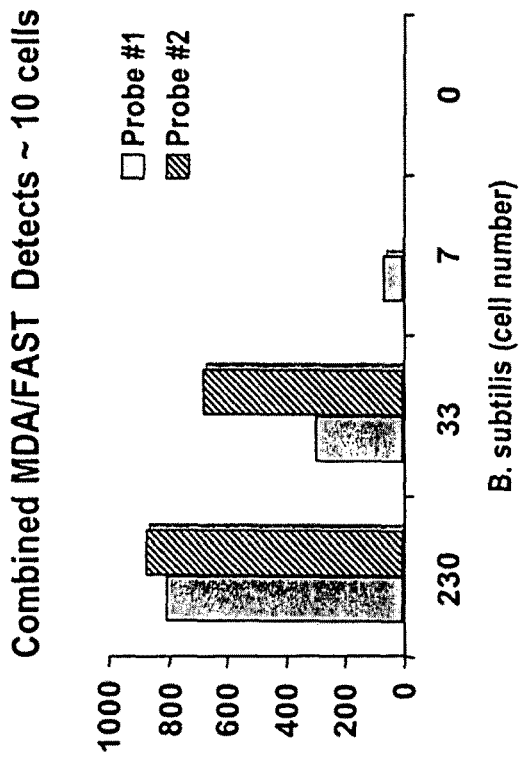
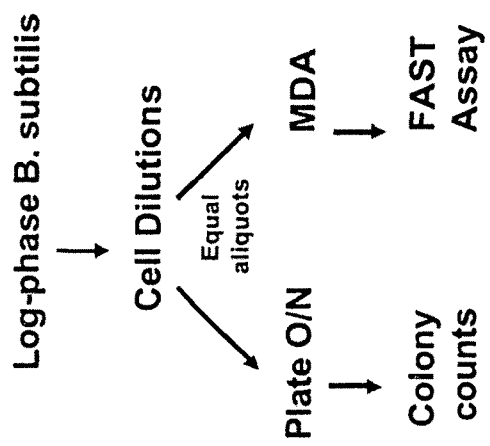

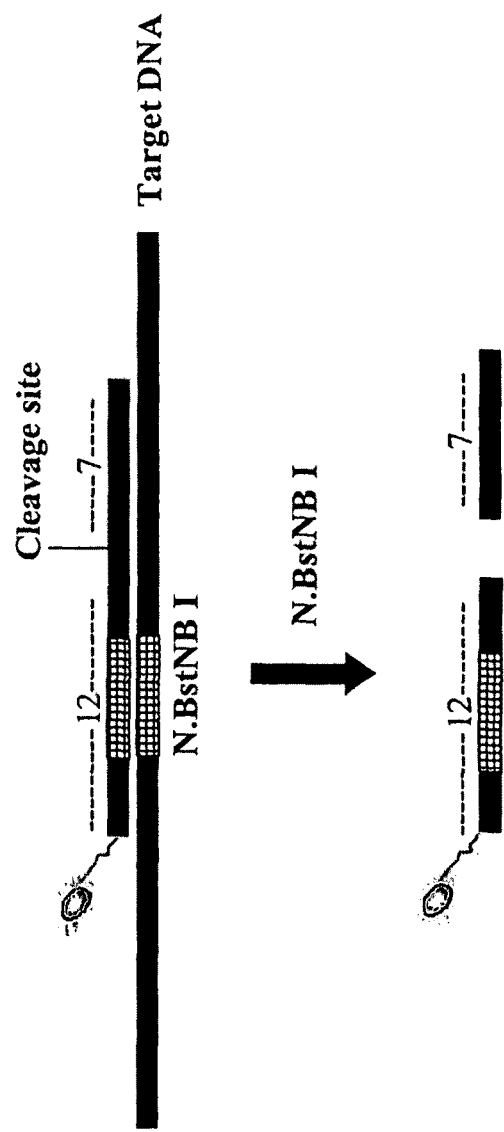

US 9,012,142 B2

SEQUENCE-SPECIFIC DETECTION OF NUCLEOTIDE SEQUENCES

CROSS-REFERENCE TO PRIORITY/PCT/PROVISIONAL APPLICATIONS

This application claims priority under 35 U.S.C. §119 of U.S. Provisional Application Nos. 60/652,743, filed Feb. 15, 2005, and 60/758,196, filed Jan. 12, 2006, and is a 371 of PCT/US 2006/005248, filed Feb. 15, 2006, and designating the United States (published in the English language on Aug. 24, 2006, as WO 2006/088910 A2), each hereby expressly incorporated by reference in its entirety and each assigned to the assignee hereof.

GOVERNMENT SUPPORT

Work described herein was funded, in whole or in part, by the United States Army RDECOM Acquisition Center under contract number W911SR-05-C-0029. The United States Government may have certain rights in this invention.

BACKGROUND OF THE INVENTION

1. Technical Field of the Invention

The present disclosure relates to methods for the detection of specific nucleotide sequences and reagents and kits for use in practicing the methods.

2. Description of Background and/or Related and/or Prior Art

The methods disclosed herein provide novel methods that utilize nicking endonuclease enzymes. Such enzymes have been previously described. For example, U.S. Pat. No. 6,191,267 discloses recombinant DNA encoding a nicking endonuclease, N.BstNBI, and the production of N.BstNBI restriction endonuclease from the recombinant DNA utilizing PleI modification methylase. U.S. Pat. No. 6,395,523 discloses two methods to engineer nicking endonucleases from existing Type IIs restriction endonucleases, and the production of engineered nicking endonucleases. One approach involves inactivating the dimerization function of a Type IIIs restriction enzyme using site-directed mutagenesis approach. Another approach involves replacing the cleavage domain of a Type IIs restriction enzyme with the cleavage domain from the naturally occurring nicking endonuclease, N.BstNBI.

SUMMARY OF THE INVENTION

A method for detecting the presence of a target nucleotide sequence in a sample of DNA can comprise exposing a test sample comprising single stranded DNA to a DNA probe and a nicking endonuclease under conditions that would permit sequence-specific hybridization of the probe to a complementary target sequence, wherein the probe comprises a sequence complementary to the target sequence that also includes a recognition sequence for the nicking endonuclease; and, observing whether the probe is cleaved by the nicking endonuclease, wherein the presence of probe cleaved by the nicking endonuclease indicates the presence of the target nucleotide sequence in the sample DNA. In various embodiments, the method can be multiplexed to detect the presence of a plurality of target nucleotide sequences in a sample of DNA. In alternative embodiments, the method can further comprise producing amplified DNA from a biological sample. These and other variations are set forth in greater detail below.

BRIEF DESCRIPTION OF THE DRAWINGS

FIG. 1. Overview of the streaming probe technique 1.

FIG. 3. Detection of E. coli 16S DNA in the presence of an excess of nonspecific DNA.

FIG. 4A. Schematic representation of a streaming reaction with Nt. Alw I adapted for CE or gel analysis.

FIG. 5. Detection of specific DNA sequences in E. coli genomic DNA. A. Analysis of the reactions using P/ACE MDQ LIF. B. The scale was expanded to more clearly show the peaks corresponding to the 5mers.

FIG. 6. Schematic of the effect of single point mismatches between probe and target on the streaming reaction.

FIG. 8. Results showing the sensitivity of a combined MDA and streaming probe assay.

FIG. 10A. Schematic representation of a streaming reaction with N.BstNB I adapted for CE or gel analysis. In this example the probe is 19 nucleotides long with a fluorescein at the 5' end. N.BstNB I cuts 5 residues from the 3' end to give a 12mer and a 7mer.

Figure 2A:
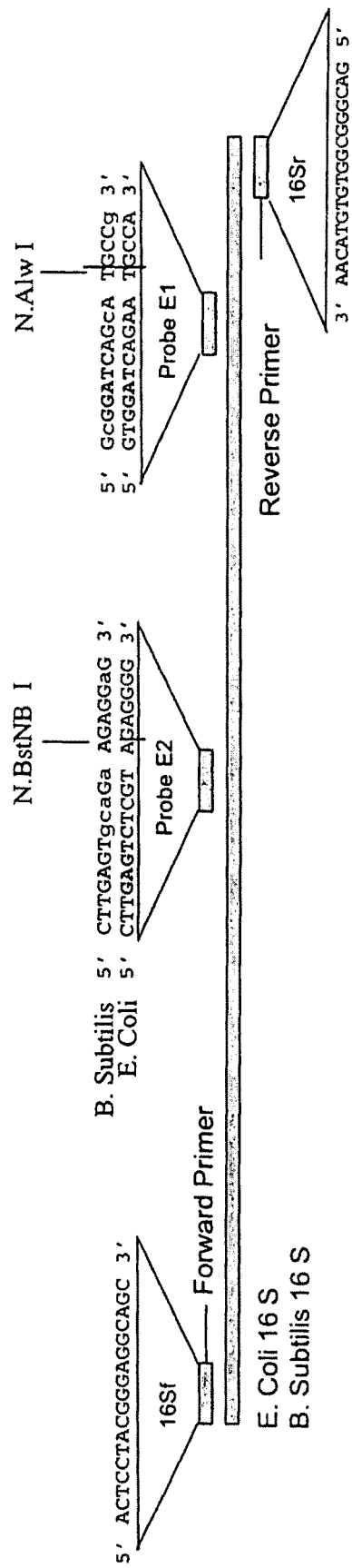
FIG. 2a. Amplification by PCR of 16S rRNA gene DNA from E. coli and B. subtilis genomic DNA and the design of the E. coli-specific probe E1 (SEQ ID NOS 1-6 are disclosed respectively in order of appearance).

DETAILED DESCRIPTION OF BEST MODE AND SPECIFIC/PREFERRED EMBODIMENTS OF THE INVENTION

We have developed a sensitive method of identifying specific single- or double-stranded DNA sequences and, by extension, other nucleic acids such as RNA that can be converted to DNA. The method involves sequence-specific hybridization of a complementary oligonucleotide probe to a target DNA. When annealed, the oligonucleotide and target create a recognition site for a strand-specific nicking restriction endonuclease. The nicking endonuclease cleaves the oligonucleotide into two pieces, but leaves the target intact. Due to the decreased size of the fragments, their affinity for target DNA is reduced and they dissociate leaving the target free to form a new complex with full-length probe oligonucleotide. The reaction contains excess oligonucleotide (on a mole to mole basis) and so hybridization, cleavage, and dissociation occur many times. The reaction is limited only (at least theoretically) by the availability of oligonucleotide and the stability of the enzyme. Because of the possibility of continuous reaction and turnover of the probe, the assay can be called a streaming probe assay and the probes referred to as streaming probes.

The reaction can be highly specific since it requires complete complementarity between the oligonucleotide and the target at the restriction site to allow restriction cleavage and can be conducted so as to require complete or nearly complete complementarity outside of the enzyme recognition site to allow hybridization. Hybridization temperatures can be adjusted to allow increased or decreased specificity; sequences containing just one mismatch (e.g., single nucleotide polymorphisms (SNPs)) can be distinguished if desired.

Any technique that can determine the presence of different sized or cleaved DNA can be used to measure either the rate or the end point of the streaming assay reaction. For example, in one embodiment, denaturing polyacrylamide gel electrophoresis (PAGE) is a relatively simple technique that can be used to detect cleavage of the probe oligonucleotide. In another embodiment, the method can be made exceptionally sensitive by using fluorescently labeled DNA together with capillary electrophoresis (CE). In yet another embodiment, a real time method can be performed using an oligonucleotide comprising a fluorescent group attached at one end and a quencher on the other end of the oligonucleotide. In this case, cleavage and dissociation of the probe results in increased fluorescence that can be measured in real-time using a fluorescence reader. As one example, we demonstrate that a streaming assay can be used to specifically detect the presence of plasmids, such as *Bacillus anthracis* pX01 and pX02 plasmids, *E. coli* genomic DNA and *Bacillus subtilis* genomic DNA.

The method can be used whenever there is a desire to detect a specific sequence that includes a recognition sequence of a nicking restriction endonuclease that is known or can be engineered from a type IIs restriction endonuclease. For instance, this method is suitable for detecting the presence of specific DNAs in a mixture (microorganism contamination, infection, etc.); and it can be used for SNP analysis and for genotyping. Statistically, one or more unique target sites containing a suitable nicking endonuclease recognition sequence can be expected to be found in most all DNA sequences of sufficient length.

When combined with whole genome amplification (WGA), for example using isothermal multiple displacement amplification (MDA), it is possible specifically detect genomic DNA amplified from about ten bacterial cells or less. The streaming probe assay can be multiplexed allowing the detection of multiple sequences (multiple genes in one organism or individual genes in multiple organisms). The multiplexing system can be noncompetitive in nature, unlike multiplexing systems that use polymerase chain reaction (PCR), and allows the generation of high throughput quantitative data.

A method utilizing WGA and a streaming probe can have significant advantages over current methods such as PCR. These can include the following. There is no need to purify DNA before amplification. Amplified DNA is generated that can be used directly with the streaming probe. DNA that can be used for thousands of streaming probe reactions is generated at once. Both DNA amplification and detection methods can be nondestructive, i.e., the same DNA can be used for multiple sequential tests including forensic tests.

The methods described herein exploit the particular properties of nicking restriction endonuclease enzymes. When conventional restriction endonucleases bind to their recognition sequences in DNA, they hydrolyze both strands of the DNA duplex at the same time. Two independent hydrolytic reactions proceed in parallel, driven by the presence of two catalytic sites within each enzyme, one for hydrolyzing each DNA strand. That is, restriction enzymes classically recognize a double-stranded DNA binding site and then cleave each strand of the DNA using two independent catalytic cleavage centers. Nicking endonucleases, on the other hand, cut only one strand. Nt.BstNB I is a naturally occurring nicking endonuclease that only cleaves one strand due to its inability to form dimers (4,5). The nicking endonuclease Nt.Alw I was engineered by creating a fusion protein between the DNA binding domain of Alw I and the cleavage/dimerization domain of Nt.BstNB I (6). Three additional nicking endonucleases Nt.BbvC I, Nb.BbvC I and Nb.Bsm I have been created. The methods described herein exploit the single-strand cleavage activities of nicking endonucleases to provide a sensitive assay for detecting the presence of specific sequences in a DNA sample, or any sample that can be converted to DNA containing a nicking site. In principle, the assay will work with any nicking endonuclease.

Five nicking endonucleases are now available from New England Biolabs. N.BstNB I occurs naturally and nicks by virtue of its inability to form dimers. N.Alw I, a derivative of the restriction enzyme Alw I, has been engineered to behave in the same way. Both nick just outside their recognition sequences. N.BbvC IA and N.BbvC IB are alternative derivatives of the heterodimeric restriction enzyme BbvC I, each engineered to possess only one functioning catalytic site. These two enzymes nick within the recognition sequence but on opposite strands. Nb.Bsm I cleaves only one strand of DNA on a double-stranded DNA substrate. Nicking endonucleases are as simple to use as restriction endonucleases.

As disclosed in U.S. Pat. No. 6,395,523, it is possible to engineer known restriction enzymes to hydrolyze only one strand of the duplex, i.e., to produce DNA molecules that are "nicked," rather than cleaved. Therefore, it is possible to create new specificities as desired from the array of known enzymes and the methods described herein can be generally applied to any sequence for which an appropriate restriction endonuclease exists or can be engineered. The method is not limited to use of Nt.Alw I, Nt.BstNB I, Nb.Bsm I, and Nt.BbvC I, which are exemplified herein.

Thus, a method for detecting the presence of a target nucleotide sequence in a sample of DNA can comprise:

exposing a test sample comprising single stranded DNA to a DNA probe and a nicking endonuclease under conditions that would permit sequence-specific hybridization of the probe to a complementary target sequence, wherein the probe comprises a sequence complementary to the target sequence that also includes a recognition sequence for the nicking endonuclease; and, observing whether the probe is cleaved by the nicking endonuclease, wherein the presence of probe cleaved by the nicking endonuclease indicates the presence of the target nucleotide sequence in the sample of DNA.

The probe need not be perfectly complementary to the target, except in the recognition sequence. Hybridization conditions, can be chosen by the skilled practitioner to provide a desired degree of sequence specific hybridization. In various embodiments, one or more base mismatches may be permitted, or perfect complementarity may be required.

FIG. 1 illustrates an exemplary scheme for carrying out the method. Sample DNA comprising a target sequence is first denatured in the presence of a molar excess of an oligonucleotide probe (any method of denaturation should work, heat denaturation was used herein). This probe contains a nicking endonuclease recognition sequence (black bar) and is complementary to one strand of the target DNA. 2. The probe anneals to the target reforming the nicking endonuclease site. 3. On the addition of nicking enzyme, the probe is cleaved and the reduced affinity of the two resulting oligonucleotides allows them to dissociate from the target. Fresh full-length probe hybridizes with the target and is cleaved; the process repeats. In the example shown, the oligonucleotide probe is labeled with a fluorescent tag on the 3' end and a fluorescence quencher on the 5' end (alternate positions are possible as long as the fluor and quencher are separated at the end of the reaction, and the position does not inhibit enzymatic cleavage). Cleavage of the probe results in separation of the fluorescent tag and quencher resulting in increased fluorescence that can be detected in real time. The use of a fluorescence tag-quencher pair is not essential. Any method that can measure the presence of cleaved probe is sufficient. The optimum reaction temperature will vary based on the temperatures at which the oligonucleotide probe and cleavage products dissociate from the target under the enzymatic buffer conditions (i.e., the melting temperature ($T_m$)) and the nicking endonuclease used.

Observing whether or not the probe is cleaved can be accomplished by any technique that can observe the presence of shortened DNA probes or the cleavage of a fluorescently labeled probe, including poly-acrylamide gel electrophoresis (PAGE), capillary electrophoresis (CE), and fluorescence resonance energy transfer (FRET). Of these three techniques, CE is the most sensitive. However, FRET analysis can be performed in a real-time streaming assay. Fluorescent labels and quenchers can be placed anywhere in the probe, the only constraint being that they must not inhibit the nicking endonuclease. For instance, two fluorescent labels can be used to increase the signal strength, or probes with different spectral characteristics can be used in multiplexing.

There are other possible ways of detecting the fragments. Other optical detection methods may be used including bioluminescence and phosphorescence techniques, with or without resonance transfer (e.g., BRET and PRET). In addition, lanthanide-based energy transfer (LRET) may be used to observe the separation between appropriate labels. Another possibility is to use Mass Spectroscopy with or without mass spectroscopy tags. Another possible method is Raman Spectroscopy. Indeed, labeling of the probe with a surface enhanced Raman sphere can increase sensitivity many fold. Another way to detect the fragments produced relates to the fact that each cleavage results in a new 3' hydroxyl and a new 5' phosphate. The increasing presence of either can be measured and enzymatic activity calculated.

Both single and double stranded DNA can be a target for the assay. Indeed, any DNA molecule that can be made single stranded should work in principle. Furthermore, with some nicking endonucleases, direct detection of RNA will be possible (7). An enzyme that recognizes and cuts RNA/DNA hybrids would work as in FIG. 1 with the substitution of DNA target with RNA target (any kind of RNA). An alternative would be to perform an initial reverse transcriptase step to produce cDNA before the streaming reaction. Yet a third way to detect RNA would be to construct a nicking endonuclease that contains a polynucleotide binding site that binds to RNA/DNA hybrids. These kinds of constructs work well with restriction endonucleases (8) so they should also work when fused with the nicking activity of a nicking endonuclease.

Probes can be of any suitable length as may be chosen by a skilled practitioner with consideration of several factors including the following. Probes will be preferably chosen that are of sufficient length to permit sequence specific hybridization and sufficiently short to permit release of the cleaved probe. The skilled practitioner will recognize that the ideal length will be a function of the melting temperature ($T_m$) of the full-length probe and the $T_m$'s of the two products. That is, the $T_m$ differential will preferably be sufficient to allow initial hybridization of the probe followed by subsequent dissociation of both probe fragments. Where convenient, these considerations can be circumvented by cycling temperatures between a reaction/annealing phase and a dissociation phase. In exemplary embodiments employing temperature cycling, the reaction/annealing phase can be conducted at about 40° C. to about 50° C., preferably about 43° C. to about 47° C., most preferably about 45° C., and the dissociation phase can be conducted at about 50° C. to about 60° C. or at most the limit of stability for the nicking endonuclease, for example preferably at about 53° C. to about 58° C., e.g., at about 55° C. However, in general it is to be expected that assays can be designed by choosing a probe/target/enzyme combination that permits use of a single temperature at which the whole reaction proceeds efficiently without having to cycle temperatures. Indeed, in preferred embodiments, using nicking enzymes at near their maximum temperature limit (e.g., 58° C. for Nt.Alw I) yields very fast and sensitive assays.

Probes can be labeled with any appropriate labels possessing detectable optical, mass, or resonance signatures and the like for use in any of the techniques described herein and similar measurement methods. In positioning the labels, care is preferably taken to avoid labeling a probe in any position that will substantially impair the functioning of the nicking enzyme.

There are currently 5 nicking enzymes available. However, methods of engineering additional specificities have been developed and described. Indeed DNA binding domains other than those from restriction enzymes can be used (8). A temperature resistant nicking endonuclease that would be compatible with PCR may be engineered. One can then perform real-time PCR with a streaming probe and the requirement for an exact sequence match when using these enzymes should reduce false positive rates.

The system is very amenable to multiplexing. In one embodiment, a fluorescent group can be positioned relative to the restriction site in different probes so that different sized fluorescent oligonucleotides are formed from different targets. Alternatively, dyes with different spectral characteristics can be used in probes for different targets.

A streaming assay as described herein works well on DNA amplified by multiple displacement amplification. In exemplary embodiments, amplification occurs first and then the streaming reaction is run. However, it should be relatively simple to perform the two assays simultaneously. The probe can be modified so that it can not act as a primer and is resistant to the 3' to 5' exonuclease of the Phi29 polymerase. In preferable embodiments, both reactions run at the same temperature. Conventionally, MDA is performed at 30° C. And, the streaming assay is preferably performed at about 45 to 59° C. However, judicious modification of annealing temperatures and/or buffer conditions and use of alternative polymerase enzymes should permit use of a single temperature.

These methods can be useful in many applications, including: detection and identification of specific organisms in antibioterrorism efforts, medical applications for human and animal health, strain/species analysis e.g., ecological studies; molecular biology methods including in situ creation of a signal in a semi-fixed environment such as on a surface or in a gel, creation of a large amount of a specific oligonucleotide from a larger one, sequence-specific activation—e.g., where cleavage product(s) but not the parent (probe) is biologically active, sequence-specific inhibition—where cleavage removes a biological activity of the probe, detection and quantization of levels of DNA or RNA in any system including biological systems or extracts, in vitro assays and the like; and, genomic analyses including SNP/mutation analysis/genotyping. Test samples can include environmental sources such as air (aerosol sampling) water, soil and the like; biological sources can include serum, ascites fluid, cerebrospinal fluid, amniotic fluid, synovial fluid, pleural fluid, saliva, sputum, stool, urine, semen, tissue, biopsies, swabs, and the like from human and non-human sources. The methods can be used to detect sequences in RNA and the samples can comprise RNA, for example including viruses having RNA genomes. In such cases, the methods described herein can comprise preparing DNA from the sample by reverse transcription. The method can be sued to detect a wide variety of bacteria, viruses and parasites, such as fungi, protozoa, helminthes, and the like.

The following examples serve to further illustrate various aspects and embodiments of the methods described herein. These examples should not be considered limiting in any way.

EXAMPLES

Materials and Methods

The following materials and methods are used in the examples below unless otherwise indicated.

Genomic DNA. Genomic *E. coli* and *B. subtilis* genomic DNAs were supplied by Molecular Staging Incorporated and were generated using MDA (9) from 100 *E. coli* cells using their REPLI-g® kit. Real-time polymerase chain reaction (PCR) was used to assess the purity of the genomic DNAs (not shown). *B. subtilis* DNA was also generated in house using Qiagen's REPLI-g® kit. Genomic DNA from all other organisms was generated using Qiagen's REPLI-g® kit. The identity of the genomic DNA was confirmed by PCR-sequencing.

PCR amplified DNA for use in streaming assay reactions. The 16 S genes from *E. coli* and *B. subtilis* were amplified by PCR using the primers 16Sf (1) and 16Sr (2). Single stranded 16S DNA was prepared using single primer (16Sr) PCR and the amplicon. PCR primers were designed on sequences within the *E coli* (E-oligonucleotides) or *B subtilis* (B-oligonucleotides) 16S RNA genes. PCR reactions were set up using the DyNAzyme PCR reaction kit (MJ Research) with 25 pmoles primers and with 30 cycles (1 min @ 94° C., 1 min @ 55° C., 1 min @ 72° C.) proceeded by a 10 min @ 95° C. denaturation step and followed by a 8 min @ 72° C. extension step.

Oligonucleotides. Oligonucleotides used in these examples are shown in Table 1. Nicking endonuclease sites are in bold, mutations from the wild-type sequence are in lower case. E probes; *E.coli* based; B probes, *Bacillus subtilis* based; c probes, complement of a probe sequence.

TABLE 1

(SEQ ID NOS 7-33 respectively in order of appearance):
Oligonucleotide Probes

N.Alw I Probes and Complements (c)

| | |
|---|---|
| E1 | GT GGATC AGAATGCCA |
| E1c | TGGCATTCT GATCC AC |
| B1 | GC GGATC AGCATGCCG |
| B1c | CGGCATGCT GATCC GC |
| B2 | CC GGATC TGAGGTAACGATGT |
| E1c m1 | aGGCATTCT GATCC AC |

TABLE 1-continued (SEQ ID NOS 7-33 respectively in order of appearance):
Oligonucleotide Probes

| | |
|---|---|
| E1c m2 | TcGCATTCT GATCC AC |
| E1c m3 | TGcCATTCT GATCC AC |
| E1c m4 | TGGgATTCT GATCC AC |
| E1c m5 | TGGCtTTCT GATCC AC |
| E1c m6 | TGGCAaTCT GATCC AC |
| E1c m7 | TGGCATaCT GATCC AC |
| E1c m8 | TGGCATTgT GATCC AC |
| E1c m9 | TGGCATTCa GATCC AC |
| E1c m10 | TGGCATTCT cATCC AC |
| E1c m11 | TGGCATTCT GtTCC AC |
| E1c m12 | TGGCATTCT GAaCC AC |
| E1c m13 | TGGCATTCT GATcC AC |
| E1c m14 | TGGCATTCT GATCg AC |
| E1c m15 | TGGCATTCT GATCC tC |
| E1c m16 | TGGCATTCT GATCC Ag |

N.BstNB I probes and Complements (c)

| | |
|---|---|
| E2 | CTT GAGTC TCGTAGAGGGG |
| E2c | CCCCTCTACGA GACTC AAG |
| B2c | CTCCTCTTCTG CACTC AAG |

Nt.BbvC I probe

| | |
|---|---|
| BB-1 | AATTAT CCTCAGC GCCTTT |

PCR 16 S amplicon Probes

| | |
|---|---|
| 16Sf | ACTCCTACGGGAGGCAGC |
| 16Sr | GACGGGCGGTGTGTACAA |

Nicking Endonucleases. Table 2 summarizes the nicking endonucleases used in these examples. All nicking endonucleases were obtained from New England BioLabs. Reaction conditions were as suggested by the manufacturer. The amount of enzyme, target DNA, and oligonucleotide probe used, and the length, temperature and volume of the reaction, varied from experiment to experiment and are given in the text and/or figure legends.

TABLE 2

| | | Streaming Assay | |
|---|---|---|---|
| Nicking Enzyme | Recognition Site | Complement | MDA |
| Nt.ALW I | 5 bp | YES | YES |
| Nb.BSM | 6 bp | YES | YES |
| Nt.BbvC I | 7 bp | YES | YES |

PAGE Samples were separated on a 20% polyacrylamide, 7 M urea gel using a standard procedure (3).

Fluorescence assays using a FRET probe. Oligonucleotides were constructed that had a 5' fluorescence quencher (Iowa black, IDT) and a 3' fluorescent group, Alexa 488. Probe streaming reactions were performed in a multi-well plate and analyzed on a SpectraMax Gemini EM, Molecular Devices' fluorescence plate reader using an excitation wavelength of 484 nm and an emission wavelength of 525 nm. The relative fluorescence units shown represent the actual readings minus background fluorescence.

Fluorescence assays using Capillary Gel electrophoresis. Oligonucleotides were constructed that had either a 5 or a 3' fluorescein group. Two instruments were used for this analysis, either a Beckman P/ACE MDQ LIF or an AB1 3130XL. Electrokinetic loading was used in all cases. For the Beckman P/ACE MDQ LIF instrument, the distance from the loading point to the detector was either 20 cm or 10 cm depending on the experiment and the eCAP ssDNA 100-R kit from Beckman was used with voltages between 9,000 and 30,000 volts and loading times of 2 to 10 seconds. In analyses using the ABI 3130XL, the POP6 polymer was used on a 36 cm capillary using ABI's Fragment Analysis Protocol.

Example 1

FRET-based Streaming Assay

In the streaming assay, as in the non-streaming assay, the oligonucleotide probe is cleaved into two shorter products. There are a number of ways of measuring this cleavage. One way is to measure the change in fluorescence resonance energy transfer between a donor and an acceptor fluorescent moieties, or a fluorescent moiety and a quencher, arranged on opposite side of the cleavage site on a probe, e.g., a FRET assay.

Usually, when a fluorescent molecule is activated by a certain wavelength of light it emits light (fluoresces) at a longer wavelength and this emitted light can be measured using a fluorometer. In FRET, when an acceptor or quencher is present in close proximity to a fluorescent molecule (i.e., a donor), rather than fluoresce, the energy is absorbed by the acceptor or quencher that may or may not (i.e., a dark quencher) emit light at an even longer wavelength.

By arranging a fluor moiety and a quencher moiety in each of the products of parent probe cleavage, i.e., on opposite sides of the probe cleavage site, the parent probe will be quenched due to the proximity of the fluor and quencher but not quenched in the cleaved probe products. That is, cleavage of the probe by a restriction endonuclease physically separates the quencher from the fluor, thereby reducing quenching and causing a measurable increase in fluorescence. This kind of assay is illustrated in FIG. 1. Because the acceptor or quencher may emit at a longer wavelength than the donor fluor, as alternatives to observing an increase, in the fluorescence of the fluor, it is also possible to observe a decrease in emission from an acceptor, or to observe changes in the relative intensities of emission at donor and acceptor emission wavelengths.

Target DNA is first denatured by heating at 95° C. for 10 min in the presence of a molar excess of an oligonucleotide probe (FIG. 1). The target DNA can be any DNA that is, or can be made, single-stranded. We have used oligonucleotides, PCR-amplified DNA, and genomic DNA (Materials and Methods). The probe is an oligonucleotide that has a quencher on the 5' end and a fluor on the 3' end. Although, in this example quencher and fluor are on opposite ends of the probe, either fluor or quencher can be placed anywhere within each of the fragments as long as they do not inhibit enzymatic cleavage and as long as they end up on different cleaved products (below). The probe also contains a nicking endonuclease recognition sequence (black bar) and is complementary to one strand of the target DNA; the probe anneals to the target reforming the nicking endonuclease site. On the addition of nicking enzyme, and incubation at a suitable temperature (discussed below) the probe is cleaved and the reduced affinity of the two resulting oligonucleotides allows them to dissociate from the target. Fresh, full-length probe hybridizes with the target and is cleaved. Cleavage of the probe results in separation of the fluorescent tag and quencher resulting in increased fluorescence.

Theoretically, in the presence of active enzyme the reaction should repeat continuously until near completion. The overall sensitivity of the assay is therefore largely a factor of how much fluorescent probe is available for cleavage and the background (quenched) level of fluorescence.

Example 1.1

Detection of the *E. coli* 16S rRNA Gene in Per-Amplified DNA Using the FRET-based Streaming Assay An oligonucleotide probe was developed that hybridizes to *E. coli* 16S DNA and is cleaved by Nt.Alw I. This probe has reduced binding affinity for *B. subtilis* 16S DNA due to 3 nucleotide differences between the 16 S DNA of the 2 species (Tablet, FIG. 2*a*). FIG. 2*a* shows amplification by PCR of 16S rRNA gene DNA from *E. coli* and *B. subtilis* genomic DNA and the design of the *E. coli*-specific probe E1. The forward and reverse primers are designed to amplify 16 S ribosomal DNA from many bacterial species including *E. coli* and *B. subtilis*. (Materials and Methods). The probe was designed based on the presence of a N.Alw I or N.BstNB I site and a melting temperatures between 48 and 54° C. Red letters represent the N.Alw I and N.BstNB I recognition sites. *B. subtilis* sequence that is not identical to *E. coli* sequence is shown in lower case blue.

The utility of this probe was tested using PCR-amplified 16S DNA from *E. coli* and *B. subtilis*. The amplification was performed using a set of universal primers (FIG. 2*a*).

Figure 2B:
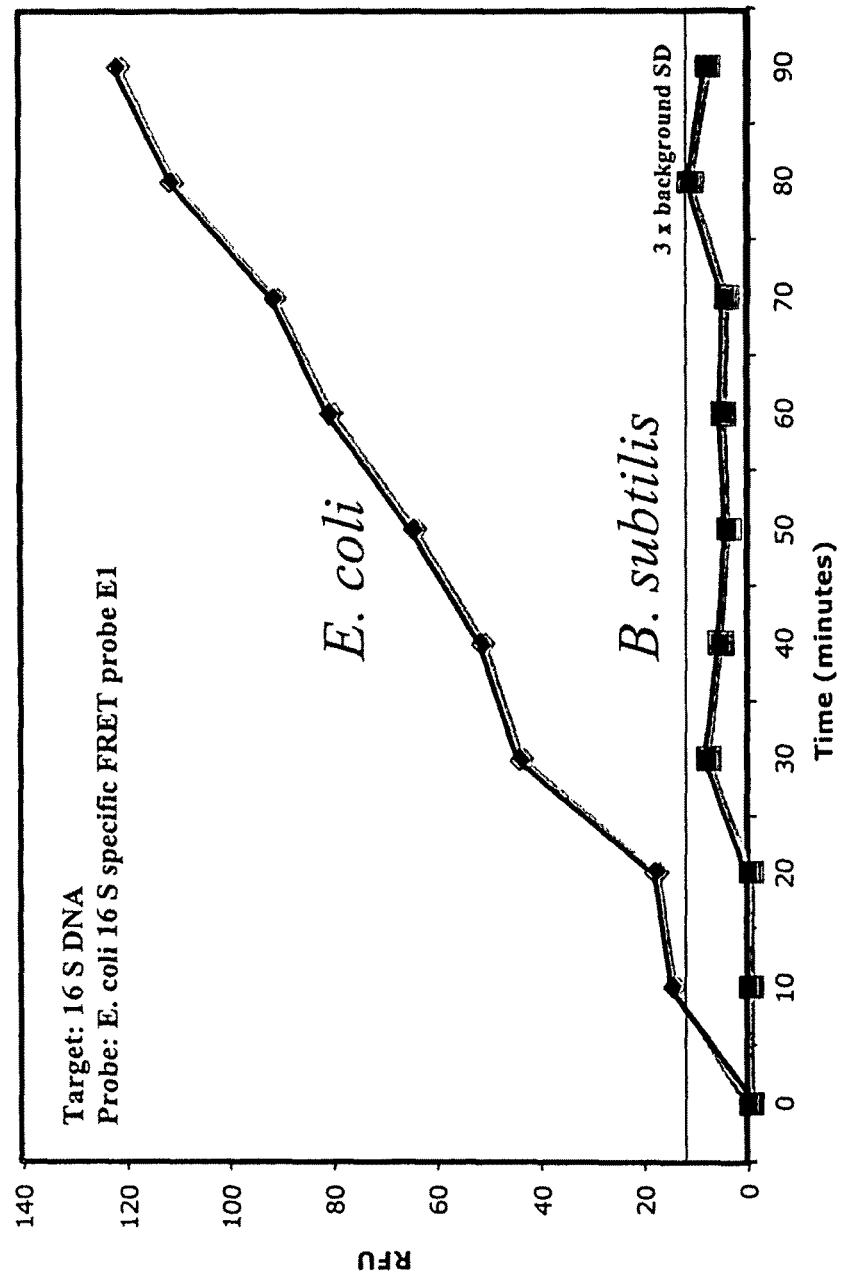
FIG. 2b. Detection of E. coli 16S Amplicon using Streaming FRET Probe Strategy.

FIG. 2*b* shows the detection of *E. coli* 16S Amplicon using a streaming FRET probe strategy. 100 fmole (65 ng) 16 S *E. coli* or *B. subtilis* DNA were incubated with 100 pmole 16S *E. coli* specific FRET probe E1, denatured at 95° C. for 10 minutes and incubated with 50 units N.Alw1 at 45° C. in a total volume of 200 µl. Fluorescence was determined at the indicated times.

As can be seen in FIG. 2*b*, starting with 100 fmoles of *E. coli* 16S amplicon, a signal above background (we used a level of 3-times the standard deviation of the background as our cut off point) can be detected. Whereas with the *B. subtilis* DNA, no signal above the cut off was detected even after 90 min. FIG. 2*b* also demonstrates that the cleavage reaction and resultant increase in fluorescence can be detected in real-time.

Example 1.2

Detection of *E. coli* 16S PCR-amplified DNA in the Presence of Excess Nonspecific DNA Using the FRET-based Streaming Assay FIG. 3 shows the detection of *E. coli* 16S DNA in the presence of an excess of nonspecific DNA. 100 fmole (65 µg) 16S rRNA *E. coli* amplicon DNA together with the indicated amounts of genomic *B. subtilis* DNA were incubated with 100 pmole 16S *E. coli* specific FRET probe E1, denatured at 95° C. for 10 minutes and incubated with 50 units Nt.Alw I in a total volume of 200 µl at 45° C. Fluorescence was determined at the indicated times.

Reactions were set up using the *E. coli* 16S amplicon and increasing amounts of 16S *B. subtilis* genomic (i.e., nonspecific) DNA (FIG. 3). We found that the addition of 5 µg of *B. subtilis* DNA to 65 ng of *E. coli* DNA resulted in little inhibition after 10 min but that this inhibition increased to about 25% after two hours. These results demonstrate that specific DNA sequences can be detected in the presence of an excess of nonspecific DNA with only a modest decrease in efficiency. In this demonstration, the excess non-specific DNA is on a weight basis and not a molar ration basis. Due to the difference in target and non-specific DNA molecule sizes the molar ratio of non-specific to target molecules is less than 1, but there is no reason to believe that the same results would not be obtained with a similar molar excess of molecules having similar sizes.

Example 2

A Simple Denaturing-acrylamide Gel-based Streaming Assay

For some applications a simple, low cost assay is most appropriate. To demonstrate such an embodiment of the method, a reaction was performed using a probe comprising a fluorescein residue at the 5' end and without a quencher residue (FIG. 4B).

Figure 4B:
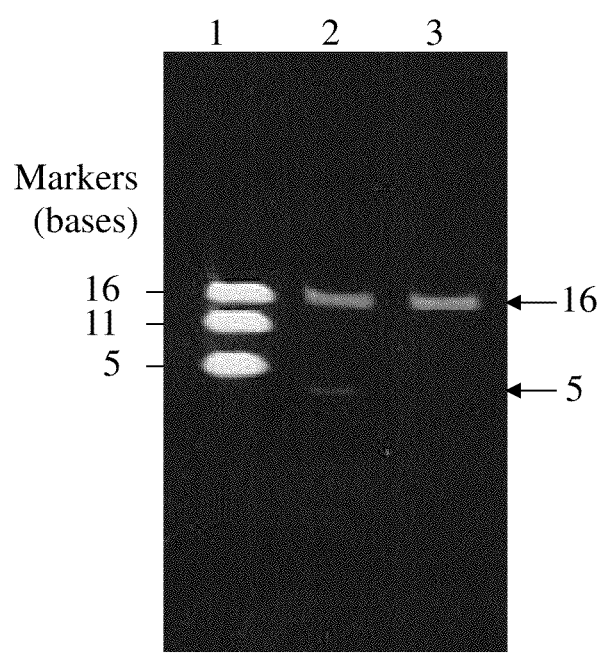
FIG. 4B. PAGE Gel showing the results of mixing 100 pmoles of the E1 probe with 100 fmoles of either E. coli (lane 2) or B. subtilis (lane 3) oligonucleotides E1c or B1c and 50 units Nt.Alw I in 50 µl buffer.

FIG. 4B shows a schematic representation of a streaming reaction with Nt.Alw I adapted for CE or gel analysis. In this example the probe is 16 nucleotides long with a fluorescein at the 3' end. Nt.Alw 1 cuts 5 residues from the 3' end to give an 11mer and a 5mer. The 5mer retains the fluorescein and can be detected using CE or PAGE (or any other technique that separates according to size).

FIG. 4B shows a PAGE gel showing the results of mixing 100 pmoles of the E1 probe with 100 fmoles of either *E. coli* (lane 2) or *B. subtilis* (lane 3) oligonucleotides E1c or B1c and 50 units Nt.Alw I in 50 µl buffer. After one hour samples were diluted 1:1 with loading buffer and 20 µl was loaded onto a 20% polyacrylamide, 7 M urea gel. Lane 1 contains marker oligonucleotides of 5, 16 and 11 residues. The gel was visualized on a UV light box. The 5mer fragment runs slightly faster than the 5mer standard because it contains a 5' phosphate (the standards do not).

The 5mer probe cleavage product is clearly visible in lane 2 where the sample comprised 100 fmoles *E. coli* complement oligonucleotide (E1c) but not in lane 3 where the sample comprised 100 fmoles *B. subtilis* complement oligonucleotide (B1c). The 11mer cleavage product is not seen because it does not retain the fluorescent label.

Example 3

A Highly Sensitive Capillary Electrophoresis (CE) Assay

Capillary electrophoresis (CE) can be used to detect probe cleavage and can provide a more sensitive alternative to the FRET assays of Example 1. CE separates charged molecules by their size and has long been used to separate DNA fragments. The Beckman P/ACE MDQ LIF system is programmable and has the ability to detect very small oligonucleotides. However, any suitable CE system can be used. The CE assay was set up in the same way as the denaturing acrylamide gel assay shown in FIG. 4B. It differs from the FRET assay in that the probe comprises a single fluorescence molecule at the 3' end of the molecule. That is, a quencher is not required and the position of the single fluorescence residue can be on the 3' or 5' ends, or internal as long as it does not inhibit endonucleolytic cleavage. Cleavage of the 16mer probe results in production of a fluorescently labeled 5mer that can be detected by CE and an unlabelled 11mer that is not observed.

Figure 4C:
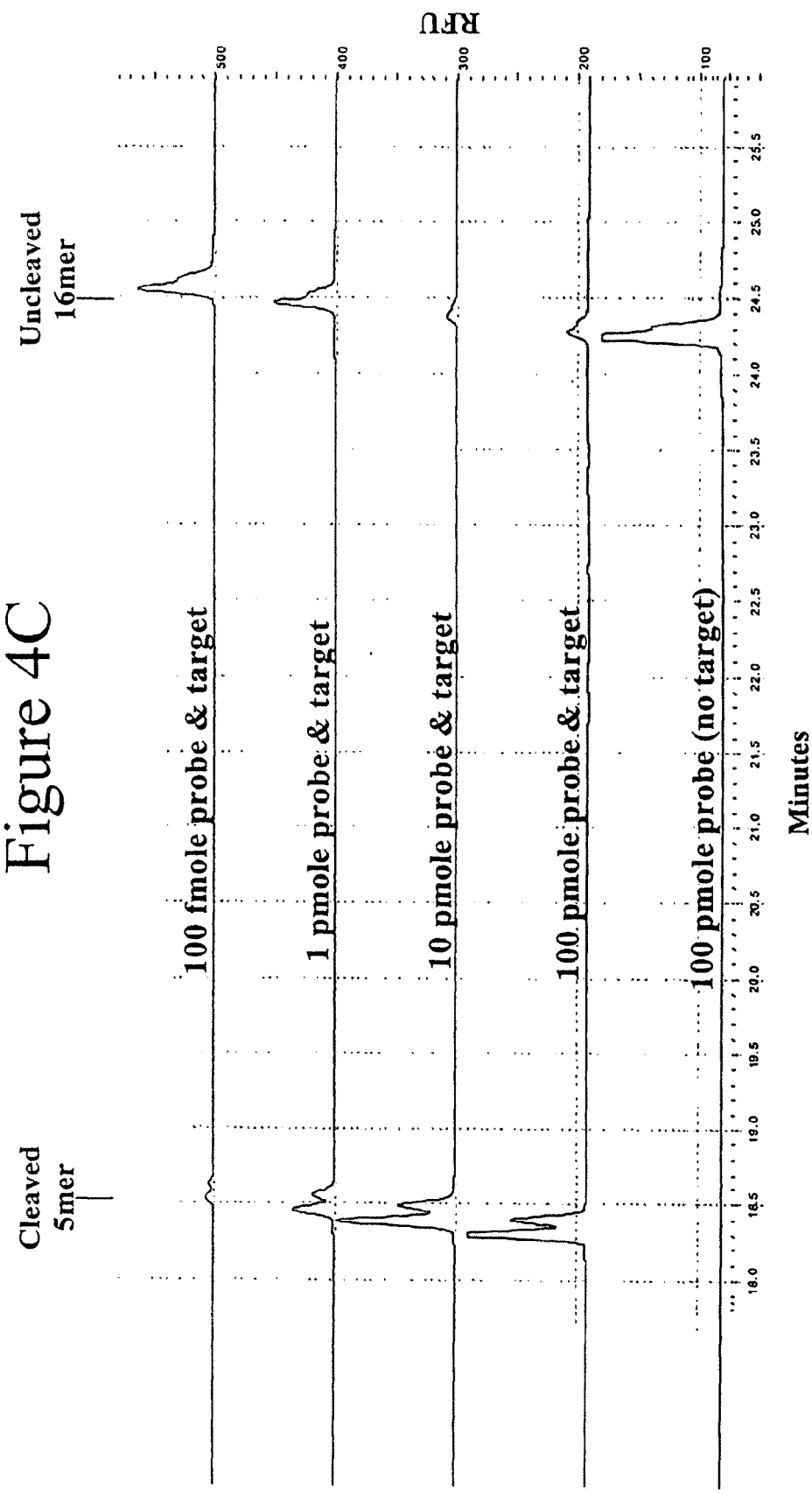
FIG. 4C. Output of a CE instrument in which E. coli complement was mixed with fluorescein labeled E1 probe in equimolar concentrations as indicated.

A CE-based assay was also used to examine the effects of varying the levels of target and probe. FIG. 4C shows the output of a CE instrument in which *E. coli* complement was mixed with fluorescein labeled E1 probe in equimolar concentrations as indicated. Samples were denatured for 10 min at 95° C. and cooled to 45° C. 50 units Nt.Alw I were added and the reaction cycled between 45° C. (1 min) and 55° C. (10 sec) for 2 hours. Samples were diluted 1000-fold and electrokinetically (5 s) loaded onto the capillary of a Beckman P/ACE and run at 9,000 volts for the time indicated. The detector was 20 cm from the loading end of the capillary. The doublet seen at the position of the 5mer is most likely a loading artifact.

Figure 4D:
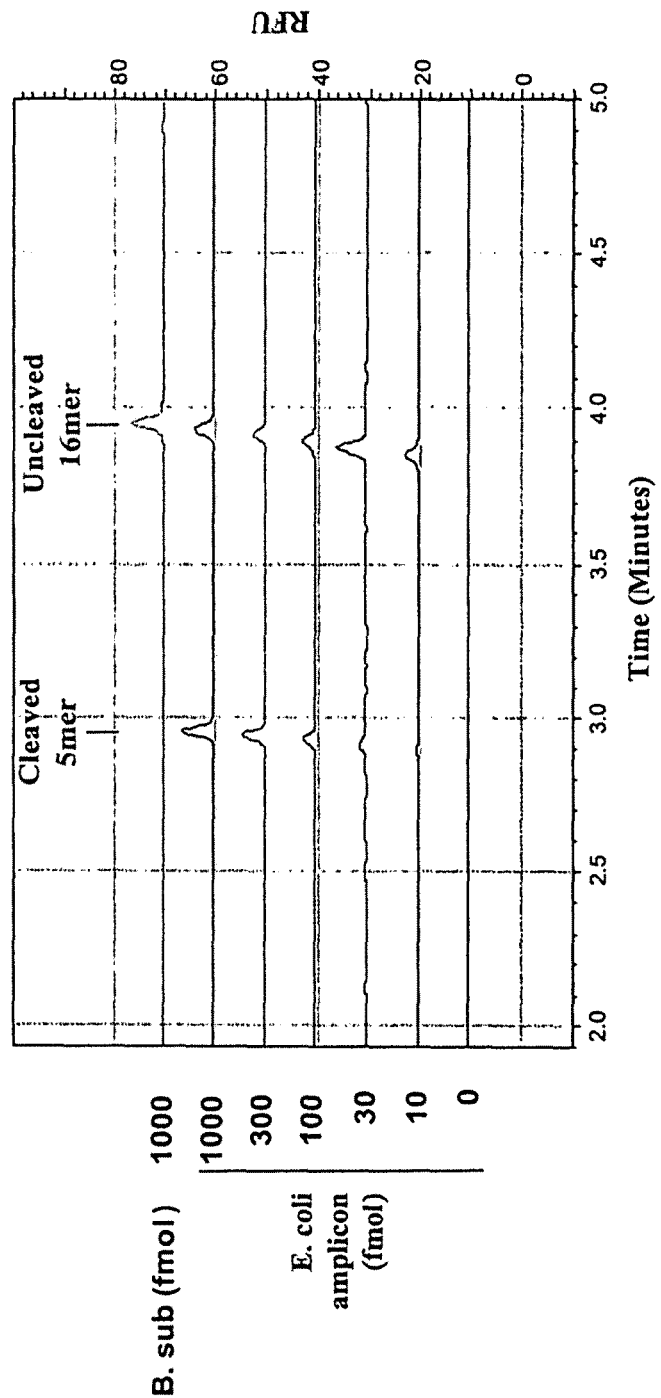
FIG. 4D. Output of a CE instrument in which E. coli or B. subtilis target 16S rRNA DNA was mixed with 100 pmole fluoroscein-labeled E1 probe as indicated in FIG. 4C.

The 5mer product eluted at about 18.4 minutes and was only seen when *E. coli* 16S amplicon was present. At levels of 100 and 10 pmoles of target and probe, nearly all the E1 probe was cleaved. As levels were reduced further there was a reduced signal but still clearly visible signal with just 100 fmoles of target and probe. The initial reaction was performed in 200 µl, and a 1 µl sample of this reaction was diluted into 100 µl before electrokinetic injection. It is expected that only a fraction of the material present in the sample enters the capillary tube. Thus the 5mer peak seen with the original 100 fmoles probe and target reaction, reflects the signal obtained from far less than 500 attomoles target. This shows a remarkable sensitivity especially given that the probe and target were in equimolar amounts rather than the probe being in excess. We also determined the effects of decreasing the amount of target while retaining a constant level of probe (100 pmoles). As can be seen in FIG. 4D, the reaction is specific. No signal is generated by 1 pmole *B. subtilis* amplicon DNA. However, as little as 10 fmoles of *E. coli* 16 S amplicon gave a positive signal.

In FIG. 4C, the 5mer elutes at approximately 18.3 minutes. To increase the speed of separation we used a 10 cm load to read setting (previously we had used 20 cm) and we increased the voltage to 30,000 from 9,000 volts. Using this set up the 5mer eluted at approximately 2.9 minutes. FIG. 4D shows the output of a CE instrument in which *E. coli* or *B. subtilis* target 16S rRNA DNA was mixed with 100 pmole fluoroscein-labeled E1 probe as indicated in FIG. 4C. Samples were denatured for 10 min at 95° C. and cooled to 45° C. Fifty units of Nt.Alw I were added (total volume 200 µl) and the reaction cycled between 45° C. (1 min) and 55° C. (10 S) for 2 hours. Samples were electrokinetically (5 sec) loaded onto the capillary of a Beckman P/ACE and run at 30,000 volts for the time indicated. The detector was 10 cm from the loading end of the capillary.

Example 3.1

Detection of *E. coli* Genomic DNA (MDA) Using the CE-based Streaming Assay

The sensitivity of the assay demonstrated in FIG. 4, indicates that the assay can be sensitive enough to detect short specific sequences within genomic DNA. To demonstrate this, we performed the assay using a Nt.Alw I probe on *E. coli* genomic DNA (Materials and Methods).

FIG. 5 shows the detection of specific DNA sequences in *E. coli* genomic DNA. Genomic DNA (0.25 µg/µl was denatured at 95° C. for 10 min in the presence of probe E1 (100 pmole). Nt.Alw 1 (50 units) was added (total volume, 200 µl) and the reaction cycled between 45° C. (1 min) and 55° C. (10 sec) for the indicated time. A. Analysis of the reactions using P/ACE MDQ LIF. Samples were diluted 1000-fold and 100 µl (25 ng genomic DNA) were subjected to a 5 sec electrokinetic loading and run at 30,000 volts. B. The scale was expanded to more clearly show the peaks corresponding to the 5mers. The position of 5 mer elution changes somewhat with repetitive CE runs due to the high voltages used. As can be seen in FIG. 5, a positive signal (the 5mer eluting at about 2.4 minutes) can be detected after a 30 min reaction. The probe used gave a positive signal with *E. colii* DNA and did not give a signal with *B. subtilis* DNA even after 120 min. This demonstrates that the streaming assay can be used to determine the presence of DNA from specific organisms.

Example 3.2

Detection of Point Mutations Using a CE-based Assay

The streaming assay can be used to distinguish between closely related DNA sequences as shown in FIG. 5. To address whether it can also be used to detect single base pair differences, we designed primers identical to the E1 complement used before but introduced a point mutation in individual oligonucleotides at each position. These oligonucleotides were then used in a streaming reaction with the E1 probe and their efficacy determined. FIG. 6 shows the effect of single point mismatches between probe and target on the streaming reaction.

Streaming reactions were set up using the *E. coli* E1 probe and targets that consisted of the perfect complement (E1c) oligonucleotide, complementary oligonucleotides each with one mismatch (m1 to m16), and a *B. subtilis* complement that has 3 mismatches (all outside of the N.Alw I binding site). Reactions were performed for 2 h and the products separated by either CE or denaturing PAGE. Black bar, no detectable cutting; vertical hash bar clearly observable product; horizontal hash bar, very low activity (the boundaries were taken as the highest temperature where a reaction was seen to occur); nucleotides in bold, Nt.Alw I site.

As can be seen in FIG. 6, a single missense mutation can be sufficient to substantially decrease the signal. Those oligonucleotides having mutations in the recognition sequence of the enzyme were completely inactive. Thus a streaming probe can be used to measure the presence of single nucleotide mutations/polymorphisms with a properly designed probe.

Example 3.3

Development of a Multiplex Assay using the ABI 3130XL

CE instruments capable of separating oligonucleotides that differ in size by one nucleotide are available. Such instruments, for example the Beckman P/ACE, can be used to perform a multiplex assay where probes that yield different lengths of cleavage product are used against multiple targets in one reaction. In such a multiplex reaction, each probe can be designed such that the cleavage site for the nicking endonuclease produces a unique sized cleavage product.

The Beckman P/ACE, is a single capillary, one-color machine so its multiplex ability is limited to distinguishing sizes. Another instrument, the ABI 3130XL, has capacity for 16 capillaries and can handle fluors of four different colors. With such a device, multiplexing assays can include probes that are labeled with different colored fluorescent moieties.

Figure 7:
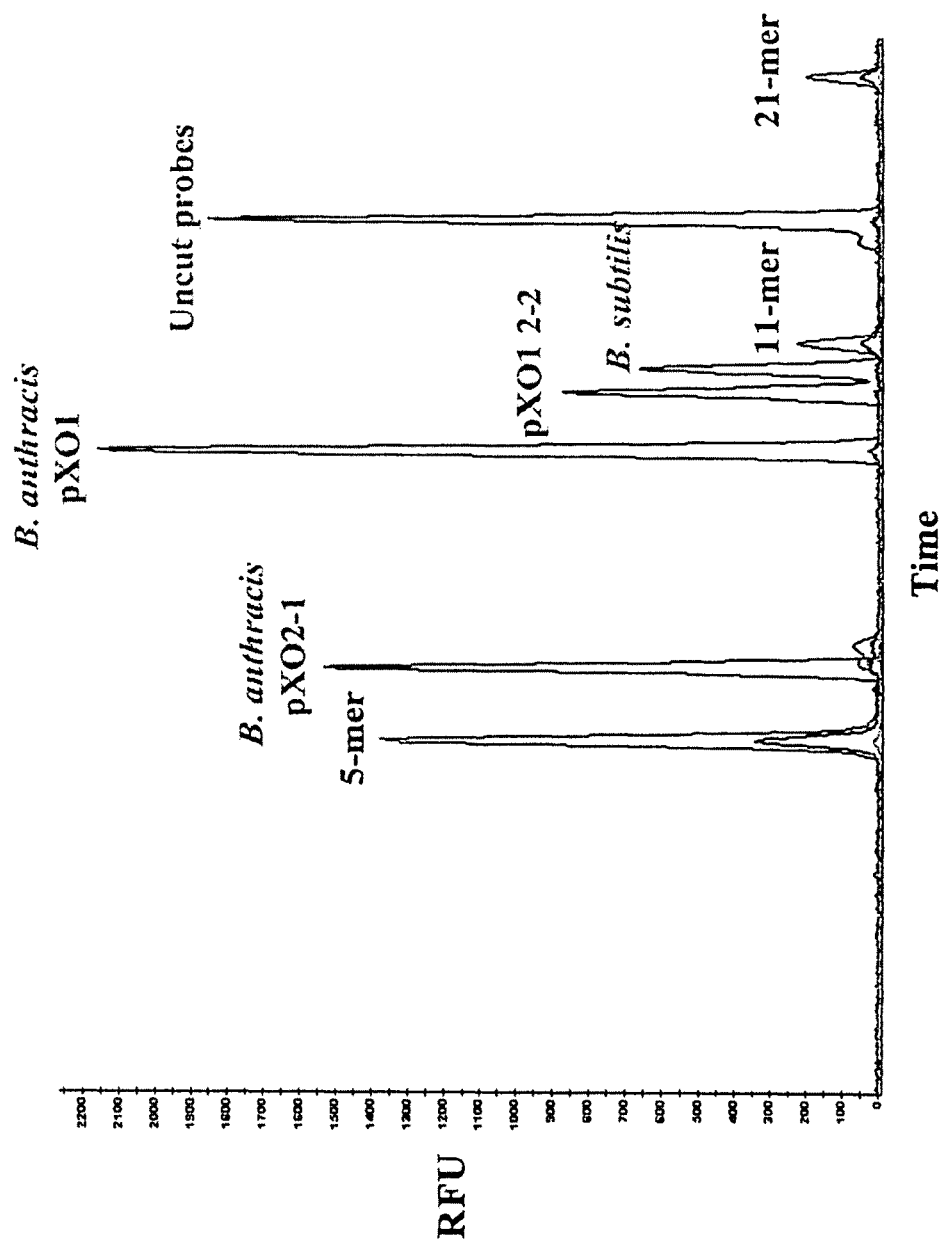
FIG. 7. Results of a four-plex assay. Probes against the four genetic elements shown were designed to give distinguishable fluorescent products using CE on an ABI 3130XL.

The results of a four-plex assay are shown in FIG. 7. In this assay, four different probes were used in one reaction. These probes were specific for the *Bacillus anthracis* plasmids pX01 and pX02 and for *Bacillus subtilis* and were designed to yield different sized cleavage products when cut by a nicking endonuclease upon hybridization. The reaction (10 µl) contained 1 pmole of each probe, 100 fmoles of each complement oligonucleotide, 10 U Nt.Alw I and 1×NEB buffer 2. The reaction was run for 1 hr. at 58° C. before analysis. The green peaks labeled in red are size standards. The *B. subtilis* probe (B2) has a fluorescein at the 5' position and gives an 11-base fragment; pX02-1 (*B. anthracis* pX02 plasmid probe) has a 3' fluorescein and yields an 10-base fragment; pX01 (*B. anthracis* pX01 plasmid probe) has a 5' fluorescein and yields an 10-base fragment; pX01 2-2 (*B. anthracis* pX01 plasmid probe) has a 5' fluorescein and yields a 11-base fragment.

In the presence of the four target DNAs, four distinct signals were generated. These data demonstrate the capability of multiplexing. Since the instrument is capable of using fluors with four different colors, a multiplex assay of 16 probes is an obvious extension. Indeed, the resolving power of the capillaries is such that multiplex assays with more than 16 probes are possible (we estimate, based on the resolving power of the capillaries, that a 40-plex is possible). These data, taken together with the above examples, also show the generality of the streaming probe, because the feasibility of the assay with three different organisms (including *E. coli*) using both chromosomal and plasmid sequences has been demonstrated.

Example 4

Use of a Combination of MDA and Streaming Probe to Detect Approximately 10 Bacteria One of the goals in applications such as detection of biowarfare agents, is to detect vanishingly small numbers of organisms. To demonstrate that the combination of MDA and streaming probe can be sensitive enough to detect low levels of bacteria, a serial dilution of a culture of *B. subtilis* was performed and the samples split into two. One half was used to quantitate the number of bacteria present; the other half was used to perform MDA.

FIG. 8 shows the sensitivity of the combined MDA and streaming probe assay. Log phase *B. subtilis* were serially diluted and each diultion was split into two. Half the dilution was used for a plating assay, while 1 µl of the other half was used for a MDA reaction (50 µl) using a REPLI-g® kit (Material and Methods). 100 ng of the amplified DNA was then used for each 10 µl streaming reaction (100 ng MDA DNA, 1 pmole probe, 10 U Nt.Alw I 58° C.). Probe 1 is B1 and probe 2 is B2 (Table 1).

As can be seen in FIG. 8, approximately 10 *B. subtilis* cells can be detected by this approach. Remarkably, the MDA reaction made enough DNA for at least 500 hundred independent streaming reactions each of which can be multiplexed if desired. These experiments show the feasibility of using this approach to detect low levels of bacteria, they also show that crude DNA produced directly from bacteria can be used for the streaming reaction.

Example 5

Adjustments in the Parameters of the Reaction

Figure 9:
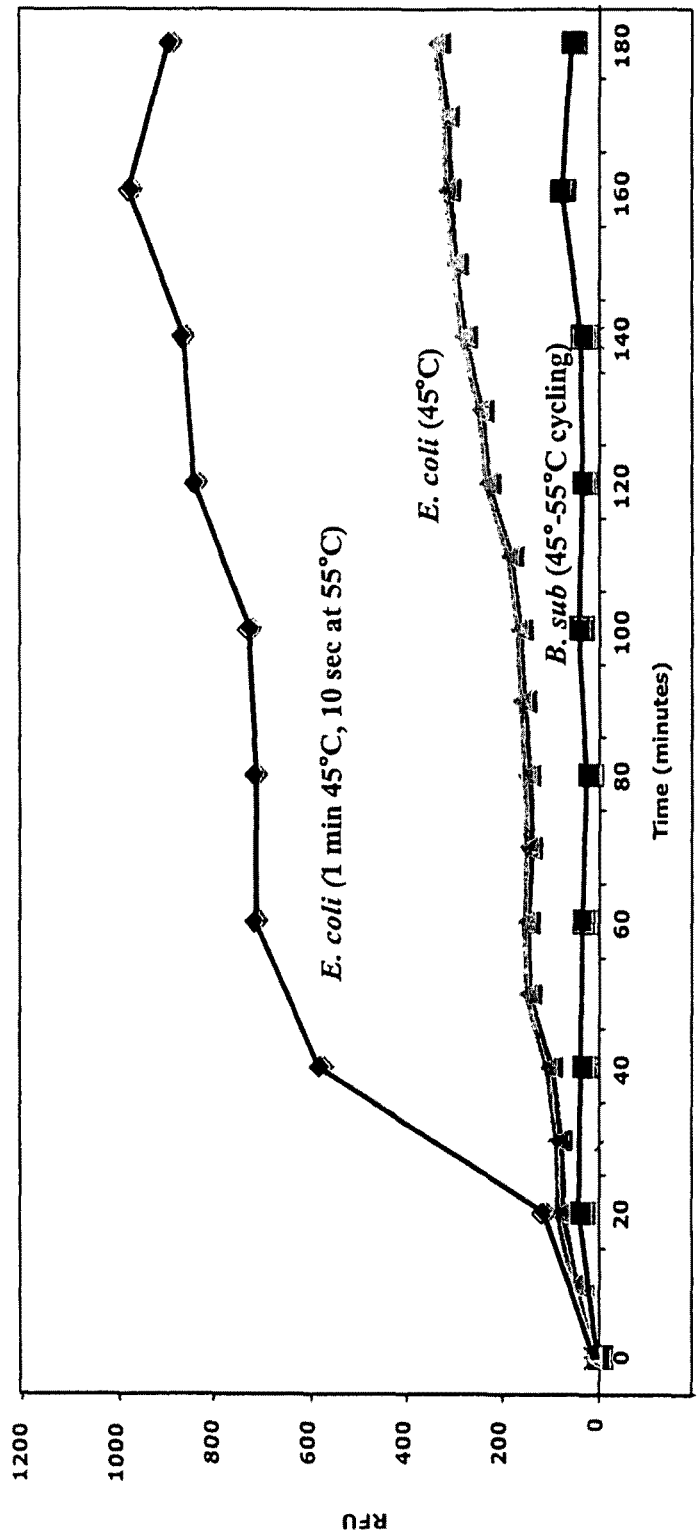
FIG. 9. Results demonstrating that cycling the temperature during annealing, cleavage and dissociation increases the reaction rate.

The Use of Temperature Cycling:

One possible rate limiting effect is the dissociation of the probe fragments from the target after the probe has undergone endonucleolytic cleavage. Indeed, as the concentration of cleaved probe increases with time, there could be a significant inhibition of the process. Initially our assays were set up at 45° C. However, cycling between two temperatures, a reaction temperature (45° C.) and a dissociation temperature 55° C. might lead to an increased rate of reaction. The results of this strategy are shown in FIG. 9. 100 fmole (65 µg) 16S *E. coli* or *B. subtilis* amplicon DNA were incubated with 100 pmole 16S *E. coli* specific FRET probe E1, denatured at 95°

C. for 10 minutes and incubated with 50 units Nt.Alw 1. At a constant 45° C. or cycled between 45° C. (1 min) and 55° C. for 10 sec.

Fluorescence was determined at the indicated times. These values were arrived at empirically. Optimal temperatures can be determined for any probe/target/enzyme combination. The results show that temperature cycling does increase the initial rate of the reaction. Nt.Alw I is stable up to at least 58° C. and at this temperature the reaction is very efficient. Temperature cycling can be of use for enzymes whose denaturation temperature is below the optimum reaction/disassociation temperature.

Use of Excess Probe:

Another possible rate-limiting step is the annealing of the probe to the target. This can be mitigated by using high concentrations of probe (pmoles) to drive the reaction forward. Interestingly, as much as practically all of the probe can be seen to be cut in assays containing as little as 1 fmole target, indicating a probe turnover of at least 1000.

Figure 10B:
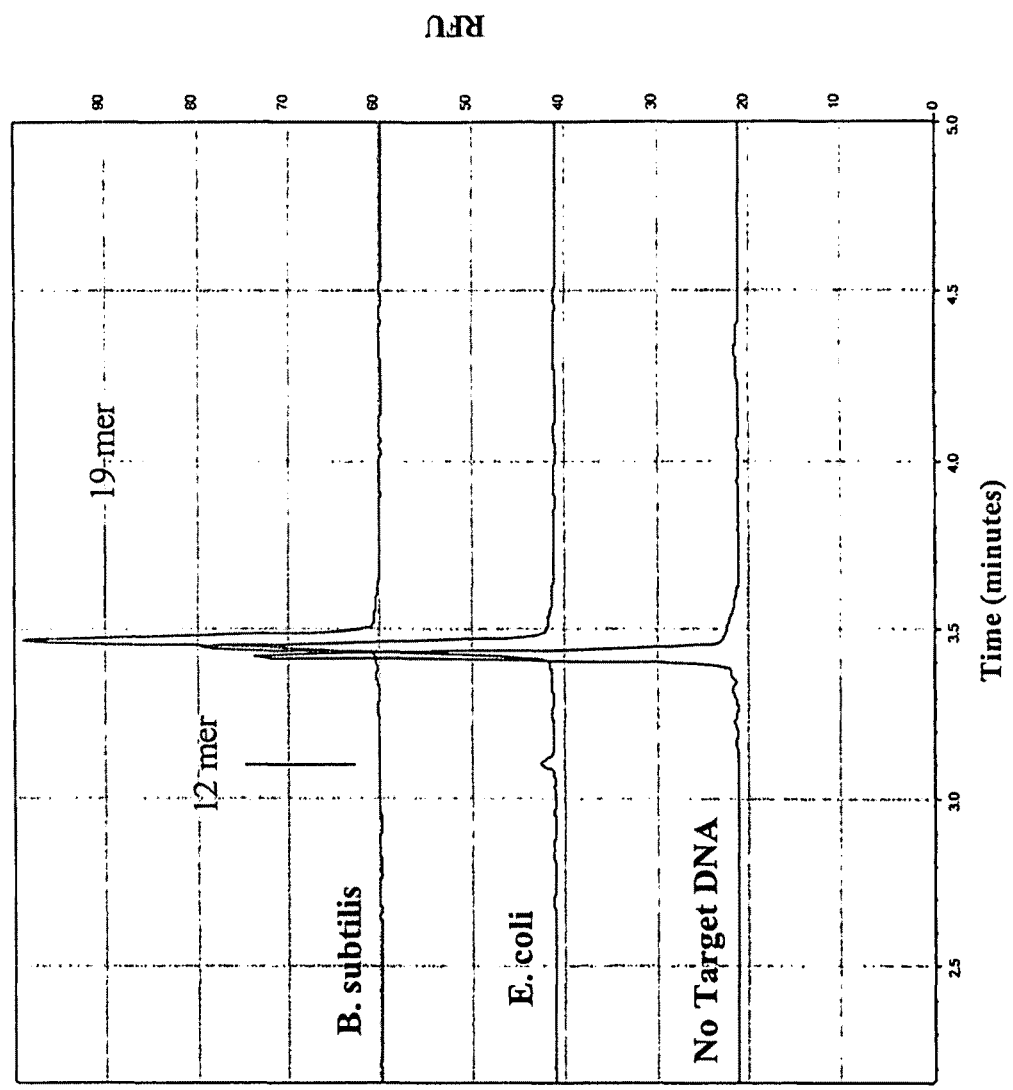
FIG. 10B. Results of a streaming assay using Nt.BstNB I.
Figure 11:
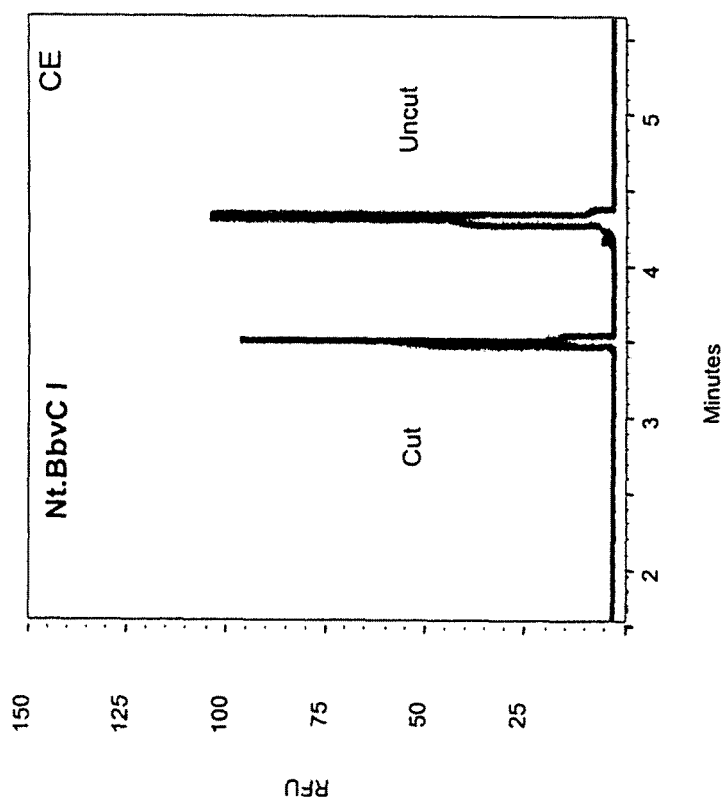
FIG. 11. Results of a Nt.BbvC I streaming assay.

Use of Other Nicking Endonucleases:

To demonstrate the generality of the method using other nicking endonucleases, a probe, E2 (FIGS. 2A, 10A) was designed to recognize the E coli amplicon and to be cleaved by Nt.BstNB I at its recognition site. FIG. 10A shows a schematic representation of the streaming reaction with N.BstNB I adapted for CE or gel analysis. In this example the probe is 19 nucleotides long with a fluorescein at the 5' end. N.BstNB I cuts 5 residues from the 3' end to give a 12mer and a 7mer. A mismatch in the N.BstNB I recognition site between E. coli and B. subtilis 16 S DNA prevents cleavage of the probe in association with B. subtilis DNA. Thus, the probe can be used to identify the E. coli target in a B. subtilis background. Detection of E. coli was tested and the results depicted in FIG. 10B. In a 200 µl reaction, 100 pmoles probe E2 were incubated with the indicated complement B2c or E2c, 100 U Nt.BstNB 1 for 2 h cycling between 45° C. for 1 minute and 55° C. for 10 sec. The sample was separated by CE with a 5 sec electrokinetic injection. The full length probe is 19 nucleotides long and is cleaved into a 12mer and a 7mer. Both the 19mer and the 12mer are seen (the 5mer is not fluorescently labeled) in the reaction containing E. coli complement DNA (E2c) but not in control reactions lacking any target or a reaction containing B. subtilis complement DNA (B2c). Similar results were obtained with the enzyme Nt.BbvCl (FIG. 11 and Table 2). 1 µg E. coli MDA was incubated with 10 pmole Nt.BbvC I probe BB-1 with a fluorescein label on the 5' end (Table 1), 10 U NT.BbvC I, in a final volume of 10 µl for 3 hrs at 54° C. The reaction was analyzed on a Beckman P/ACE.

These data show that the assay is not dependent on one nicking endonuclease but that other nicking endonucleases can be used so long as they cleave just one DNA strand.

Figure 12:
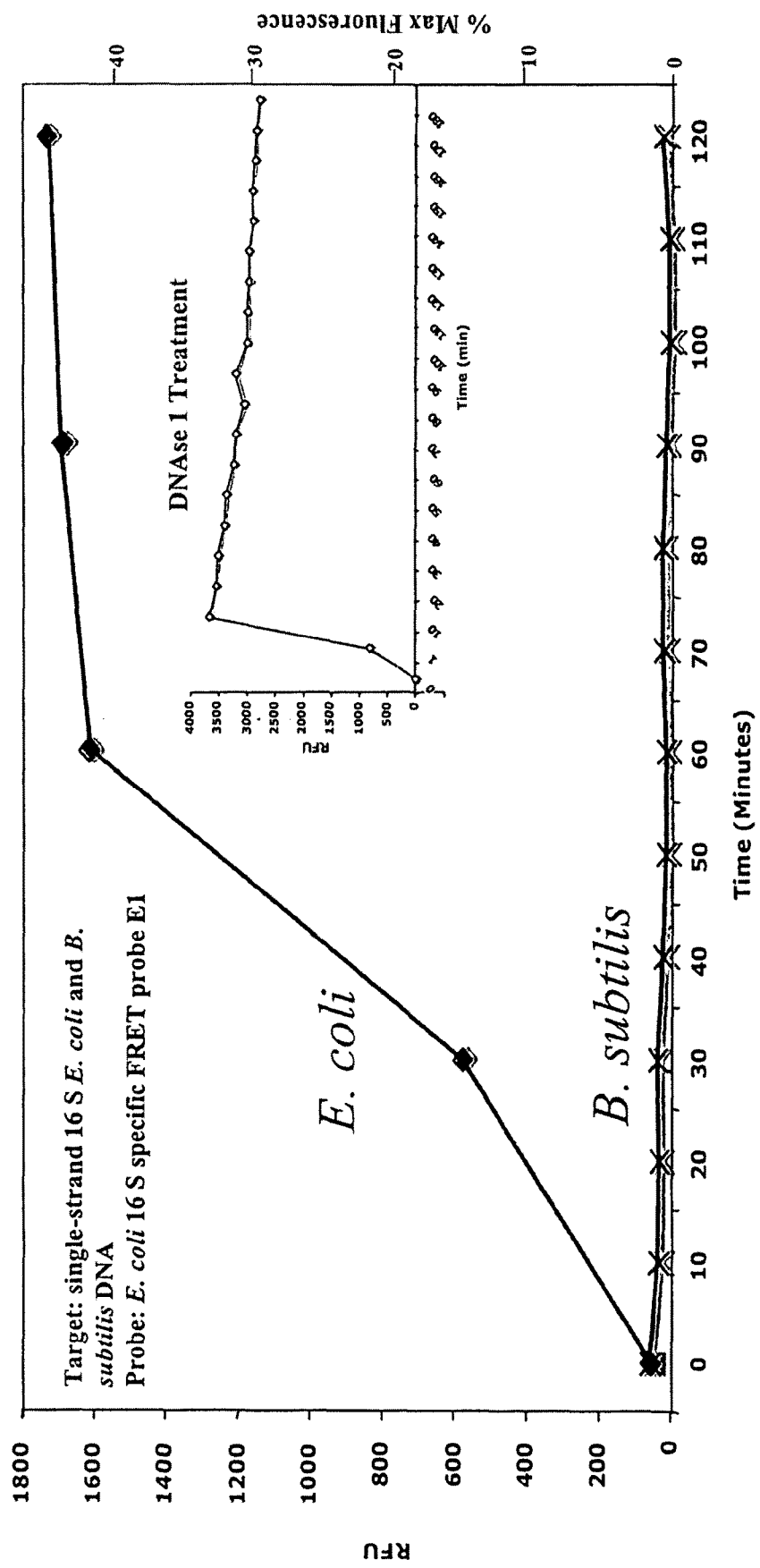
FIG. 12. Results showing that single stranded DNA target can improve sensitivity.

Detection of Single Strand Targets:

One-sided PCR was used to create a single-stranded E. coli 16 S DNA. 100 fmole (65 ng) 16 S E. coli or B. subtilis single-stranded DNA was incubated with 100 pmole 16 S E. coli specific FRET probe E1, denatured at 95° C. for 10 minutes and incubated with 50 units N.Alw 1 in a total volume of 200 µl. and cycled between 45° C. (1 min) and 55° C. for 10 sec. At the indicated times, fluorescence was determined. Inset: 100 pmole probe was incubated with 50 units of E. coli DNAse I at 37° C. Fluorescence was determined at the indicated times. As can be seen in FIG. 12, single-strand DNA works exceptionally well in the assay. To determine the maximum fluorescence possible in the assay, the reaction was treated with DNAse I and fluorescence determined over time. DNAse I cleaves all the DNA and should thus give the maximum signal possible in the reaction. The data shows that in this reaction Nt.Alw I reached a remarkable level of 45% of maximum possible fluorescence.

While the methods and articles described herein have been described with reference to specific embodiments, this application is intended to cover those various changes and substitutions that may be made by those of ordinary skill in the art.

REFERENCES

The following publications, as well as all others referenced in the disclosure, are incorporated herein by reference in their entirety:

1. Amann, R. I., Krumholz, L., and Stahl, D. A. (1990) J Bacteriol 172(2), 762-770
2. Zheng, D., Alm, E. W., Stahl, D. A., and Raskin, L. (1996) Appl Environ Microbiol 62(12), 4504-4513
3. Sambrook, J., and Russell, D. (2001) Molecular Cloning: A Laboratory Manual, Third Ed., Cold Spring Harbor Press
4. Higgins, L. S., Besnier, C., and Kong, H. (2001) Nucleic Acids Res 29(12), 2492-2501
5. Morgan, R. D., Calvet, C., Demeter, M., Agra, R., and Kong, H. (2000) Biol Chem 381(11), 1123-1125
6. Xu, Y., Lunnen, K. D., and Kong, H. (2001) Proc Natl Acad Sci USA 98(23), 12990-12995
7. Molloy, P. L., and Symons, R. H. (1980) Nucleic Acids Res 8(13), 2939-2946
8. Kim, Y. G., Shi, Y., Berg, J. M., and Chandrasegaran, S. (1997) Gene 203(1), 43-49
9. Lasken R S and Egholm M (2003) Whole genome amplification: abundant supplies of DNA from precious samples or clinical specimens. Trends Biotechnol 21, 531-535

---

What is claimed is:

1. A method for detecting the presence of a first target nucleotide sequence in a sample of single stranded DNA, comprising;
   (a) exposing the sample to a first full-length DNA probe molecule and a first nicking endonuclease under conditions that would permit sequence-specific hybridization of the first full-length probe molecule to the first target nucleotide sequence, wherein the first full-length probe molecule comprises a sequence complementary to the first target nucleotide sequence that also includes a first recognition sequence for the first nicking endonuclease with complete complementarity between the recognition sequence and the first target nucleotide sequence, whereby a first recognition site is created for the first nicking endonuclease, whereby the first full-length DNA probe molecule is cleaved into a pair of first cleaved DNA probe molecules and the first target nucleotide sequence remains intact;
   (b) disassociating the pair of the first cleaved DNA probe molecules from the first target nucleotide sequence, whereby the first target nucleotide sequence is free for hybridization;
   (c) repeating steps (a) and (b) once or more, whereby two or more pairs of the first cleaved DNA molecules are dissociated from the first target nucleotide sequence; and
   (d) detecting the dissociated two or more pairs of the first cleaved DNA probe molecules, wherein the presence of the dissociated two or more pairs of the first cleaved DNA probe molecules indicates the presence of the first target nucleotide sequence in the sample.

2. The method of claim 1, wherein the first full-length probe molecule comprises a first fluorescent moiety.

3. The method of claim 2, wherein the first full-length probe molecule further comprises an acceptor or quencher moiety that is capable of suppressing fluorescence emission from the first fluorescent moiety and is arranged on the opposite side of the first recognition sequence from the first fluorescent moiety.

4. The method of claim 3, wherein step (d) comprises observing a change in the level of the fluorescence emission.

5. The method of claim 4, wherein steps (a)-(d) are performed concurrently.

6. The method of claim 1, wherein step (d) comprises separating the first cleaved DNA probe molecules by size.

7. The method of claim 6, wherein the separation occurs electrophoretically in a polyacylamide gel.

8. The method of claim 6, wherein the separation occurs electrophoretically in a capillary.

9. The method of claim 1, further comprising:
   (a) exposing the sample to a second full-length DNA probe molecule and a second nicking endonuclease under conditions that would permit sequence-specific hybridization of the second full-length probe molecule to a second target nucleotide sequence in the sample, wherein the second full-length probe molecule comprises a sequence complementary to the second target nucleotide sequence that also includes a second recognition sequence for the second nicking endonuclease with complete complementarity between the second recognition sequence and the second target nucleotide sequence, whereby a second recognition site is created for the second nicking endonuclease, whereby the second full-length DNA probe molecule is cleaved into a pair of second cleaved DNA probe molecules and the second target nucleotide sequence remains intact;
   (b) disassociating the pair of the second cleaved DNA probe molecules from the second target nucleotide sequence, whereby the second target nucleotide sequence is free for hybridization;
   (c) repeating steps (a) and (b) once or more, whereby two or more pairs of the second cleaved DNA molecules are dissociated from the second target nucleotide sequence; and
   (d) detecting the dissociated two or more pairs of the second cleaved DNA probe molecules, wherein the presence of the dissociated two or more pairs of the second cleaved DNA probe molecules indicates the presence of the second target nucleotide sequence in the sample.

10. The method of claim 9, wherein the first and second cleaved DNA probe molecules are of different length.

11. The method of claim 9, wherein the second full-length probe molecule further comprises a second fluorescent moiety.

12. The method of claim 11, wherein the first and second fluorescent moieties have different emission wavelengths.

13. The method of claim 11, wherein the first and second fluorescent moieties have the same emission wavelength.

14. A method for detecting the presence of a target nucleotide sequence in a biological sample, comprising:
   (a) obtaining a sample of biological material;
   (b) producing amplified DNA from the biological sample;

(c) exposing the amplified DNA to a full-length DNA probe molecule and a nicking endonuclease under conditions that would permit sequence-specific hybridization of the full-length probe molecule to the target nucleotide sequence, wherein the full-length probe molecule comprises a sequence complementary to the target nucleotide sequence that also includes a recognition sequence for the nicking endonuclease with complete complementarity between the recognition sequence and the target nucleotide sequence, whereby a recognition site is created for the nicking endonuclease, whereby the full-length DNA probe molecule is cleaved into a pair of cleaved DNA probe molecules and the target nucleotide sequence remains intact;

(d) disassociating the pair of the cleaved DNA probe molecules from the target nucleotide sequence, whereby the target nucleotide sequence is free for hybridization;

(e) repeating steps (c) and (d) once or more, whereby two or more pairs of the cleaved DNA molecules are dissociated from the target nucleotide sequence; and (f) detecting the dissociated two or more pairs of the cleaved DNA probe molecules, wherein the presence of the dissociated two or more pairs of the cleaved DNA probe molecules indicates the presence of the target nucleotide sequence in the sample.

15. The method of claim 14 wherein the sample contains a pathogen and the target sequence is unique to the pathogen.

16. The method of claim 14, wherein step (b) comprises isolating RNA and producing DNA by reverse transcription.

17. The method of claim 14, wherein step (b) comprises performing whole genome amplification.

18. The method of claim 17, wherein the whole genome amplification comprises multiple strand displacement amplification.

19. The method of claim 14, wherein step (b) comprises performing multiple strand displacement amplification.

20. The method of claim 19, wherein steps (b)-(e) are performed concurrently.

21. The method of claim 20, wherein the full-length DNA probe molecule comprises a fluorescent moiety and a quencher moiety, wherein step (f) comprises observing a change in fluorescence resonance energy transfer between the fluorescent moiety and the quencher moiety, and wherein steps (b)-(f) are performed concurrently.

22. The method of claim 14, wherein the sample compromises RNA, and wherein step (b) comprises producing DNA complementary to the RNA by contacting the sample with a reverse transcriptase.

* * * * *

SEQUENCE LISTING

<160> NUMBER OF SEQ ID NOS: 33

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic probe

<400> SEQUENCE: 1
actcctacgg gaggcagc                                                 18

```
<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
cttgagtgca gaagaggag                                                     19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cttgagtctc gtagagggg                                                     19

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
gcggatcagc atgccg                                                        16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
gtggatcaga atgcca                                                        16

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
aacatgtgtg gcgggcag                                                      18

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
gtggatcaga atgcca                                                        16

<210> SEQ ID NO 8
```

```
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
tggcattctg atccac                                              16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gcggatcagc atgccg                                              16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
cggcatgctg atccgc                                              16

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
ccggatctga ggtaacgatg t                                        21

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
aggcattctg atccac                                              16

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
tcgcattctg atccac                                              16

<210> SEQ ID NO 14
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
tgccattctg atccac                                                    16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tgggattctg atccac                                                    16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tggctttctg atccac                                                    16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
tggcaatctg atccac                                                    16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
tggcatactg atccac                                                    16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
tggcattgtg atccac                                                    16

<210> SEQ ID NO 20
<211> LENGTH: 16
<212> TYPE: DNA
```

<213> ORGANISM: Artificial Sequence
<220> FEATURE:
<223> OTHER INFORMATION: Description of Artificial Sequence: Synthetic
      probe

<400> SEQUENCE: 20
tggcattcag atccac                                                       16

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
tggcattctc atccac                                                       16

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
tggcattctg ttccac                                                       16

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
tggcattctg aaccac                                                       16

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
tggcattctg atccac                                                       16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
tggcattctg atcgac                                                       16

<210> SEQ ID NO 26
<211> LENGTH: 16
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 26
tggcattctg atcctc                                                      16

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
tggcattctg atccag                                                      16

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
cttgagtctc gtagagggg                                                   19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
cccctctacg agactcaag                                                   19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
ctcctcttct gcactcaag                                                   19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
aattatcctc agcgccttt                                                   19

<210> SEQ ID NO 32
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 32
actcctacgg gaggcagc                                                        18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
gacgggcggt gtgtacaa                                                        18
```